(12) United States Patent
Antonio et al.

(10) Patent No.: US 12,213,782 B2
(45) Date of Patent: Feb. 4, 2025

(54) PHYSIOLOGICAL CHARACTERISTIC SENSOR SYSTEM

(71) Applicant: MEDTRONIC MINIMED, INC., Northridge, CA (US)

(72) Inventors: David C. Antonio, Montrose, CA (US); Juan M. Alderete, Jr., Granada Hills, CA (US); Matthew William Yavorsky, Granada Hills, CA (US); Manolo Colon Diaz, Aguadilla, OR (US); Eric Allan Larson, Simi Valley, CA (US); Shixin Chen, Simi Valley, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 329 days.

(21) Appl. No.: 16/892,854

(22) Filed: Jun. 4, 2020

(65) Prior Publication Data
US 2021/0378560 A1    Dec. 9, 2021

(51) Int. Cl.
*A61B 5/1486* (2006.01)
*A61B 5/00* (2006.01)
*A61B 5/145* (2006.01)

(52) U.S. Cl.
CPC ........ *A61B 5/14532* (2013.01); *A61B 5/1486* (2013.01); *A61B 5/6833* (2013.01);
(Continued)

(58) Field of Classification Search
CPC ... A61B 5/1455; A61B 5/14546; A61B 5/725; A61B 5/7267; A61B 5/7278; A61B 2562/0238; A61B 2562/043; A61B 5/14532; A61B 5/1486; A61B 5/6833; A61B 2560/0214; A61B 2560/0443; A61B 2560/063; A61B 2562/0223;
(Continued)

(56) References Cited

U.S. PATENT DOCUMENTS 2,551,540 A     5/1951   Johnson
4,755,173 A     7/1988   Konopka et al.
(Continued)

FOREIGN PATENT DOCUMENTS

EP    3199121 A1    8/2017
EP    3397142 B1    11/2018
(Continued)

OTHER PUBLICATIONS

PCT International Search Report and Written Opinion from International Application No. PCT/US2021/014880, dated Apr. 12, 2021, 12 pp.

*Primary Examiner* — Navin Natnithithadha
(74) *Attorney, Agent, or Firm* — Fortem IP LLP

(57) ABSTRACT

A physiological characteristic sensor system includes a physiological characteristic sensor. The physiological characteristic sensor includes a housing having a first housing portion coupled to a second housing portion, and an antenna coupled to the first housing portion. The physiological characteristic sensor system includes a sensor inserter configured to be coupled to the physiological characteristic sensor. The sensor inserter includes a sensor retainer, and the sensor retainer is configured to couple to the second housing portion in a second state to couple the physiological characteristic sensor to the sensor inserter.

19 Claims, 23 Drawing Sheets

(52) U.S. Cl.
CPC .............. *A61B 2560/0214* (2013.01); *A61B 2560/0443* (2013.01); *A61B 2560/063* (2013.01); *A61B 2562/0223* (2013.01)

(58) Field of Classification Search
CPC ........ A61B 5/68335; A61B 2560/0209; A61B 2560/0285; A61B 2560/0412; A61B 2560/045; A61B 2560/0468; A61B 2562/227; A61B 5/14503; A61B 2562/16; A61B 2562/18; A61B 2562/242; A61B 5/6849; A61B 5/14865
See application file for complete search history.

(56) References Cited

U.S. PATENT DOCUMENTS

| | | | |
|---|---|---|---|
| 5,391,250 A | 2/1995 | Cheney, II et al. | |
| 5,485,408 A | 1/1996 | Blomquist | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 6,892,085 B2 | 5/2005 | McIvor et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,468,033 B2 | 12/2008 | Van Antwerp et al. | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 7,990,320 B2 * | 8/2011 | Pros .................... H01Q 9/0421 | |
| | | | 343/702 |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 9,295,786 B2 | 3/2016 | Gottlieb et al. | |
| 10,413,183 B2 | 9/2019 | Antonio et al. | |
| 2007/0123819 A1 | 5/2007 | Mernoe et al. | |
| 2009/0299301 A1 | 12/2009 | Gottlieb et al. | |
| 2010/0160861 A1 | 6/2010 | Causey, III et al. | |
| 2011/0077480 A1 * | 3/2011 | Bloom ................... A61B 5/155 | |
| | | | 600/309 |
| 2013/0150691 A1 | 6/2013 | Pace et al. | |
| 2015/0224247 A1 * | 8/2015 | McDorman ............. A61L 2/087 | |
| | | | 206/569 |
| 2017/0112534 A1 | 4/2017 | Schoonmaker et al. | |
| 2017/0188910 A1 * | 7/2017 | Halac ................ A61B 5/14503 | |
| 2017/0251958 A1 | 9/2017 | Pushpala et al. | |
| 2017/0290533 A1 | 10/2017 | Antonio et al. | |
| 2019/0060511 A1 | 2/2019 | Larson et al. | |
| 2021/0137424 A1 | 5/2021 | Chae et al. | |
| 2021/0161437 A1 * | 6/2021 | Thomas .................... G06F 9/06 | |

FOREIGN PATENT DOCUMENTS

| | | |
|---|---|---|
| WO | 2011119896 A1 | 9/2011 |
| WO | 2012119131 A1 | 9/2012 |
| WO | 2018222015 A1 | 12/2018 |
| WO | 2019236859 A1 | 12/2019 |

* cited by examiner

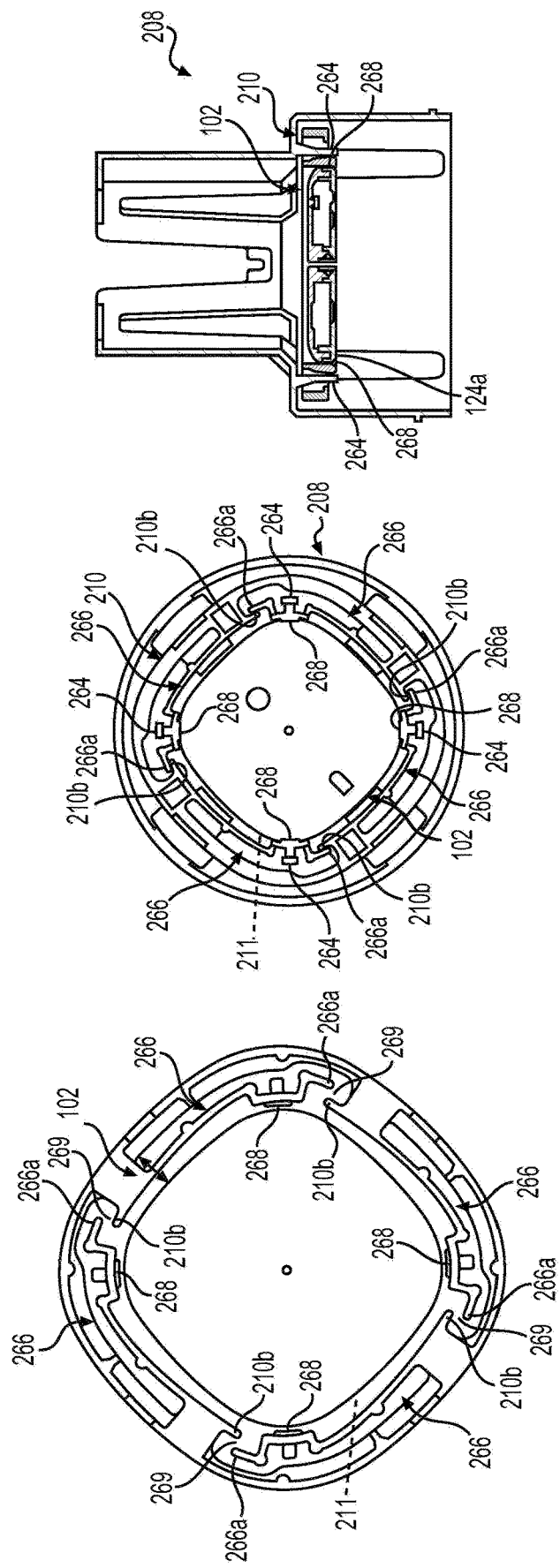

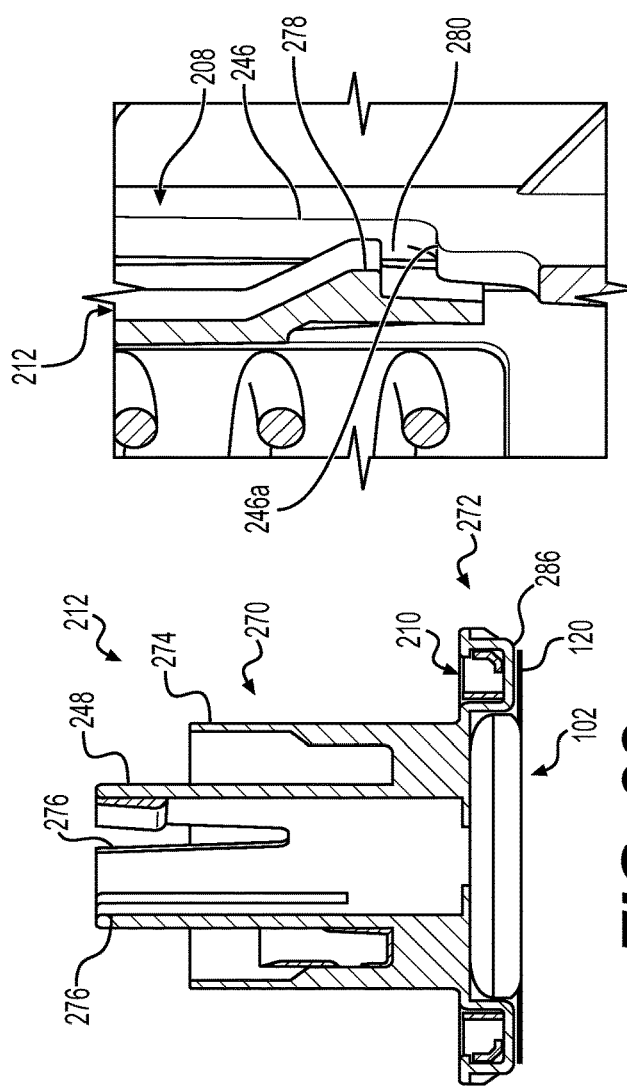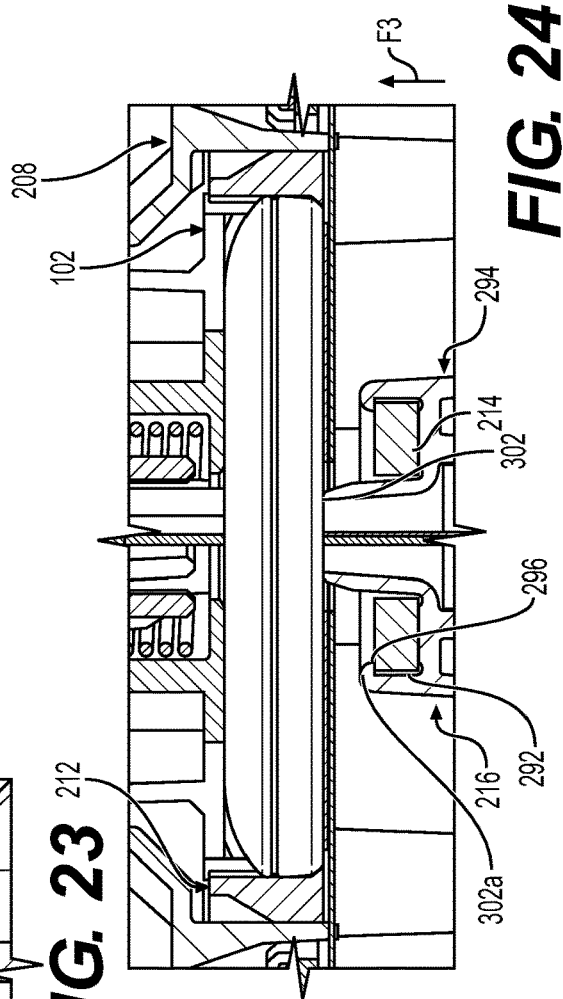

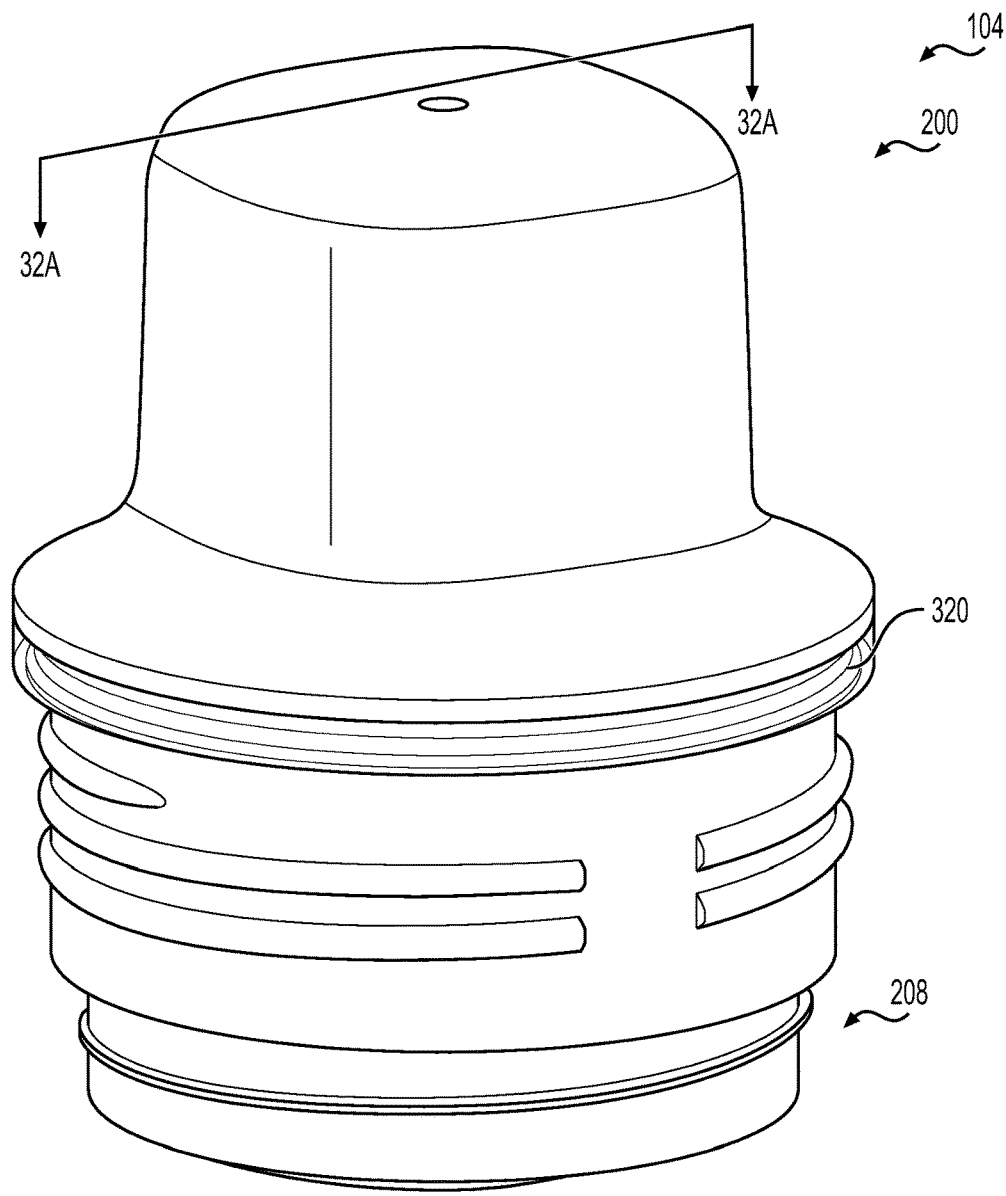
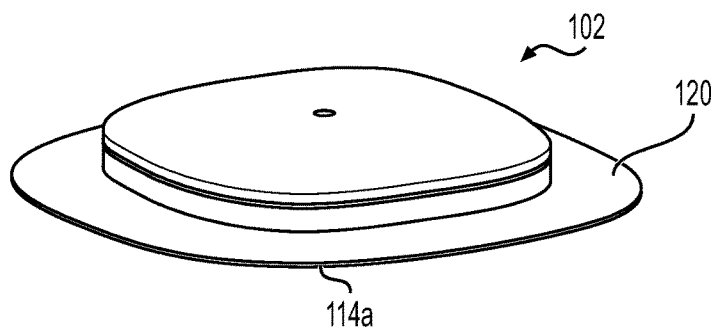
FIG. 32

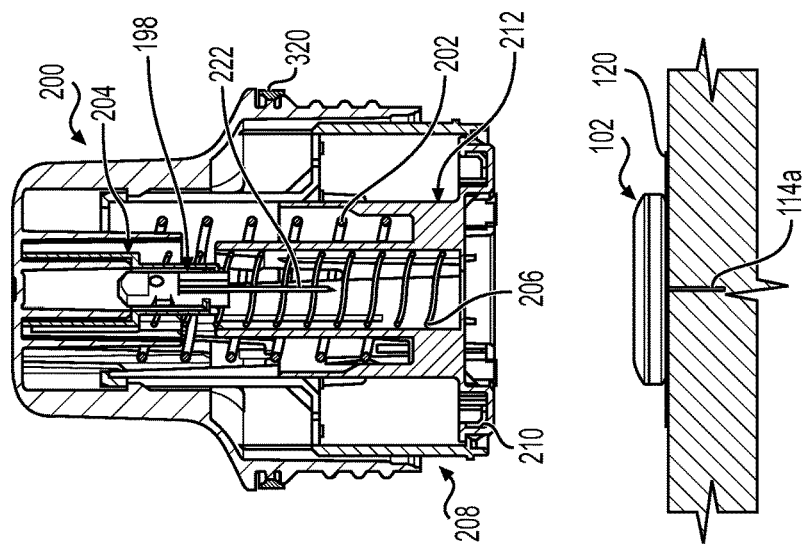
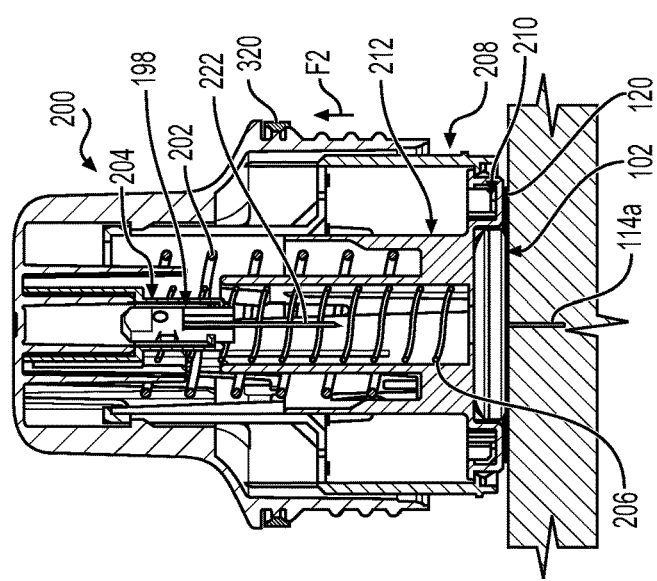
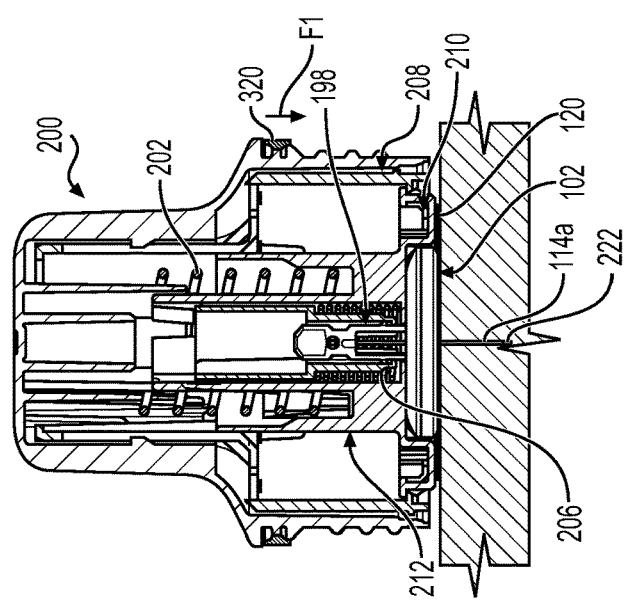

PHYSIOLOGICAL CHARACTERISTIC SENSOR SYSTEM

FIELD

Embodiments of the subject matter described herein relate generally to medical devices, such as a physiological characteristic sensor system. More particularly, embodiments of the subject matter relate to a system for a physiological characteristic sensor and a sensor inserter for coupling the physiological characteristic sensor to a user.

BACKGROUND

Sensors may be employed in the treatment of or monitoring of various medical conditions. In one example, thin film electrochemical sensors are used to test analyte levels in patients or users. More specifically, thin film sensors have been designed for use in obtaining an indication of blood glucose (BG) levels and monitoring BG levels in a diabetic user, with the distal segment portion of the sensor positioned subcutaneously in direct contact with extracellular fluid. Such readings can be especially useful in adjusting a treatment regimen which typically includes regular administration of insulin to the user.

A glucose sensor of the type described above may be packaged and sold as a product, such as a continuous glucose monitor, which is adhered to the patient during use via an adhesive skin patch. In certain instances, the continuous glucose monitor may be packaged with a sensor inserter tool, which enables the implantation of the glucose sensor subcutaneously/transcutaneously. The sensor inserter tool contains a needle that is used to puncture the skin of a user at the same time as the sensor is introduced. The needle is then withdrawn, leaving the sensor in the skin of the user.

In instances where the continuous glucose monitor is packaged with the sensor inserter tool, the sensor introducer tool may be accidently mishandled, which may affect the performance of the continuous glucose monitor and/or sensor inserter tool. In addition, as the sensor introducer tool includes a needle, it is desirable to properly dispose of the sensor inserter tool once the continuous glucose monitor has been deployed.

Accordingly, it is desirable to provide a physiological characteristic sensor system, for example, a continuous glucose monitor, which includes a glucose sensor and a sensor inserter tool that mitigates accidental mishandling and enables proper disposal of the sensor inserter tool. Furthermore, other desirable features and characteristics will become apparent from the subsequent detailed description and the appended claims, taken in conjunction with the accompanying drawings and the foregoing technical field and background.

BRIEF SUMMARY

The techniques of this disclosure generally relate to a physiological characteristic sensor system, which includes a physiological characteristic sensor and a sensor inserter for coupling the physiological characteristic sensor to a user.

According to various embodiments, provided is a physiological characteristic sensor system. The physiological characteristic sensor system includes a physiological characteristic sensor. The physiological characteristic sensor includes a housing having a first housing portion coupled to a second housing portion, and an antenna coupled to the first housing portion. The physiological characteristic sensor system includes a sensor inserter configured to be coupled to the physiological characteristic sensor. The sensor inserter includes a sensor retainer, and the sensor retainer is configured to couple to the second housing portion in a second state to couple the physiological characteristic sensor to the sensor inserter.

Also provided is a physiological characteristic sensor system. The physiological characteristic sensor system includes a physiological characteristic sensor having a housing. The physiological characteristic sensor system includes a sensor inserter configured to be coupled to the physiological characteristic sensor. The sensor inserter includes a frame, a sensor carrier and a sensor retainer. The sensor retainer is coupled to the sensor carrier and the sensor carrier is coupled to the frame. The frame has at least one rib, and the sensor retainer has at least one retainer arm that is configured to couple to the physiological characteristic sensor in a second state. The at least one rib maintains the at least one retainer arm in the second state.

Further provided is a physiological characteristic sensor system. The physiological characteristic sensor system includes a physiological characteristic sensor. The physiological characteristic sensor includes a housing having a first housing portion coupled to a second housing portion. An antenna and a first contact are coupled to the first housing portion, and a printed circuit board assembly and a battery are coupled to the second housing portion. The antenna and the battery are in communication with the printed circuit board assembly. The first contact includes a pair of spring arms that are interconnected by a body, and the body is coupled to the first housing portion such that the pair of spring arms are movable relative to the body portion. The physiological characteristic sensor system includes a sensor inserter configured to be coupled to the physiological characteristic sensor.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter. The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 17 is an end view of a sensor carrier associated with the sensor inserter, which illustrates at least one retainer arm of a sensor retainer uncoupled from the physiological characteristic sensor in a first state;

FIG. 18 is a bottom view of the sensor carrier of FIG. 17, which illustrates the at least one retainer arm of the sensor retainer coupled to the physiological characteristic sensor in a second state;

FIG. 19 is a perspective view of the sensor retainer coupled to a frame associated with the sensor inserter of FIG. 1, which illustrates at least one rib of the frame biasing the at least one retainer arm in the second state;

FIG. 22 is a cross-sectional view of the sensor carrier and sensor retainer coupled to the physiological characteristic sensor of FIG. 1;

FIG. 23 is a detail view of an insertion snap of the sensor carrier spaced apart from a surface of the frame when the sensor inserter is in a first position;

FIG. 24 is a detail view of the physiological characteristic sensor supported by a projection of a cap of the sensor inserter in the first position;

FIG. 31A is a cross-sectional view of the sensor inserter in the second position, taken along 31A-31A of FIG. 31;

FIG. 31B is a cross-sectional view of the sensor inserter in a third position, in which the physiological characteristic sensor is deployed at the insertion site and coupled to the anatomy, taken from the perspective of line 31A-31A of FIG. 31;

FIG. 32 is a perspective view of the sensor inserter in the third position, in which the senor inserter is removed from the physiological characteristic sensor at the insertion site; and FIG. 32A is a cross-sectional view of the sensor inserter in the third position, in which the sensor inserter is removed from the physiological characteristic sensor at the insertion site taken along 32A-32A of FIG. 32.

DETAILED DESCRIPTION

Figure 1:
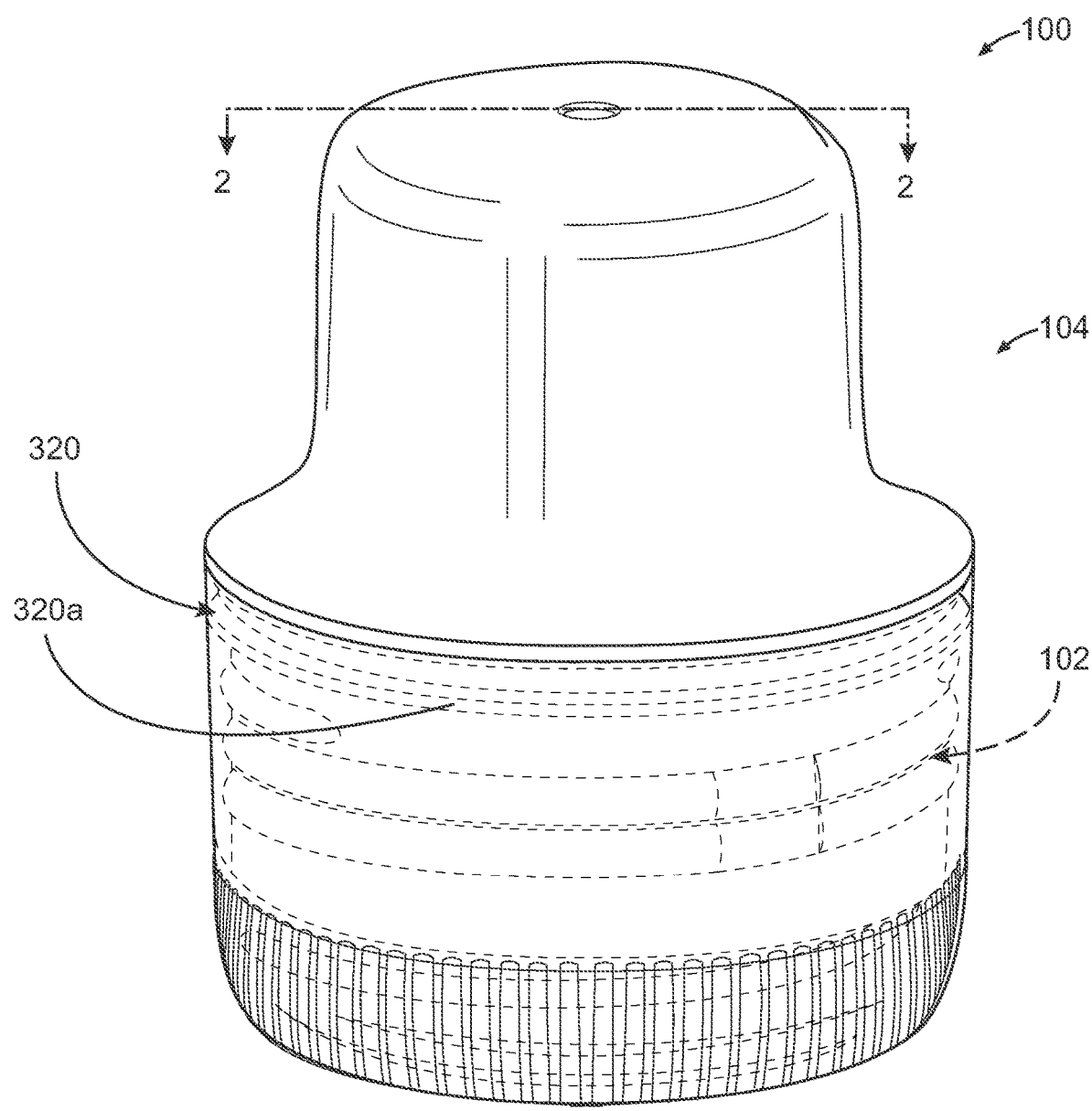
FIG. 1 is a perspective view of an exemplary physiological characteristic sensor system that includes a sensor inserter and a physiological characteristic sensor according to various teachings of the present disclosure.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominantly in the respective nominal axial or radial direction. As used herein, the term "transverse" denotes an axis that crosses another axis at an angle such that the axis and the other axis are neither substantially perpendicular nor substantially parallel.

As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of schematic, functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present disclosure may be practiced in conjunction with any number of systems, and that the physiological characteristic sensor described herein is merely exemplary embodiments of the present disclosure.

For the sake of brevity, conventional techniques related to signal processing, data transmission, signaling, control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

The following description relates to various embodiments of a physiological characteristic sensor system, which includes a physiological characteristic sensor and a sensor inserter. The systems described herein inhibit or mitigate the effects of an accidental mishandling of the sensor inserter during use, and also enable the sensor inserter to be properly disposed of once the physiological characteristic sensor is coupled to the user. It should be noted that while the physiological characteristic sensor is described herein as being a continuous glucose monitor, it will be understood that the physiological characteristic sensor may comprise a variety of other sensors, such as cardiac monitors, body temperature sensors, EKG monitors etc., medical devices, and/or other components that are intended to be affixed to the body of a user. Thus, while the non-limiting examples described below relate to a medical device used to treat diabetes (more specifically, a continuous glucose monitor), embodiments of the disclosed subject matter are not so limited.

Generally, the glucose sensor employed with the adhesive patch is a continuous glucose sensor of the type used by diabetic users. For the sake of brevity, conventional aspects and technology related to glucose sensors and glucose sensor fabrication may not be described in detail here. In this regard, known and/or conventional aspects of glucose sensors and their manufacturing may be of the type described in, but not limited to: U.S. Pat. Nos. 6,892,085, 7,468,033 and 9,295,786; and United States patent application number 2009/0299301 (which are each incorporated by reference herein). In addition, for the sake of brevity, conventional aspects and technology related to sensor inserters may not be described in detail here. In this regard, known and/or conventional aspects of sensor inserters may be of the type described in, but not limited to: U.S. Pat. No. 10,413,183 (which is incorporated by reference herein).

With reference to FIG. 1, FIG. 1 is a perspective view of a physiological characteristic sensor system 100. In one example, the physiological characteristic sensor system 100 includes a physiological characteristic sensor 102 and a sensor inserter 104. Generally, with reference to FIG. 2, the components of the physiological characteristic sensor 102 are coupled together as a single unit. The physiological characteristic sensor 102 and the sensor inserter 104 may be packaged together for use by a consumer or user.

Figure 3:
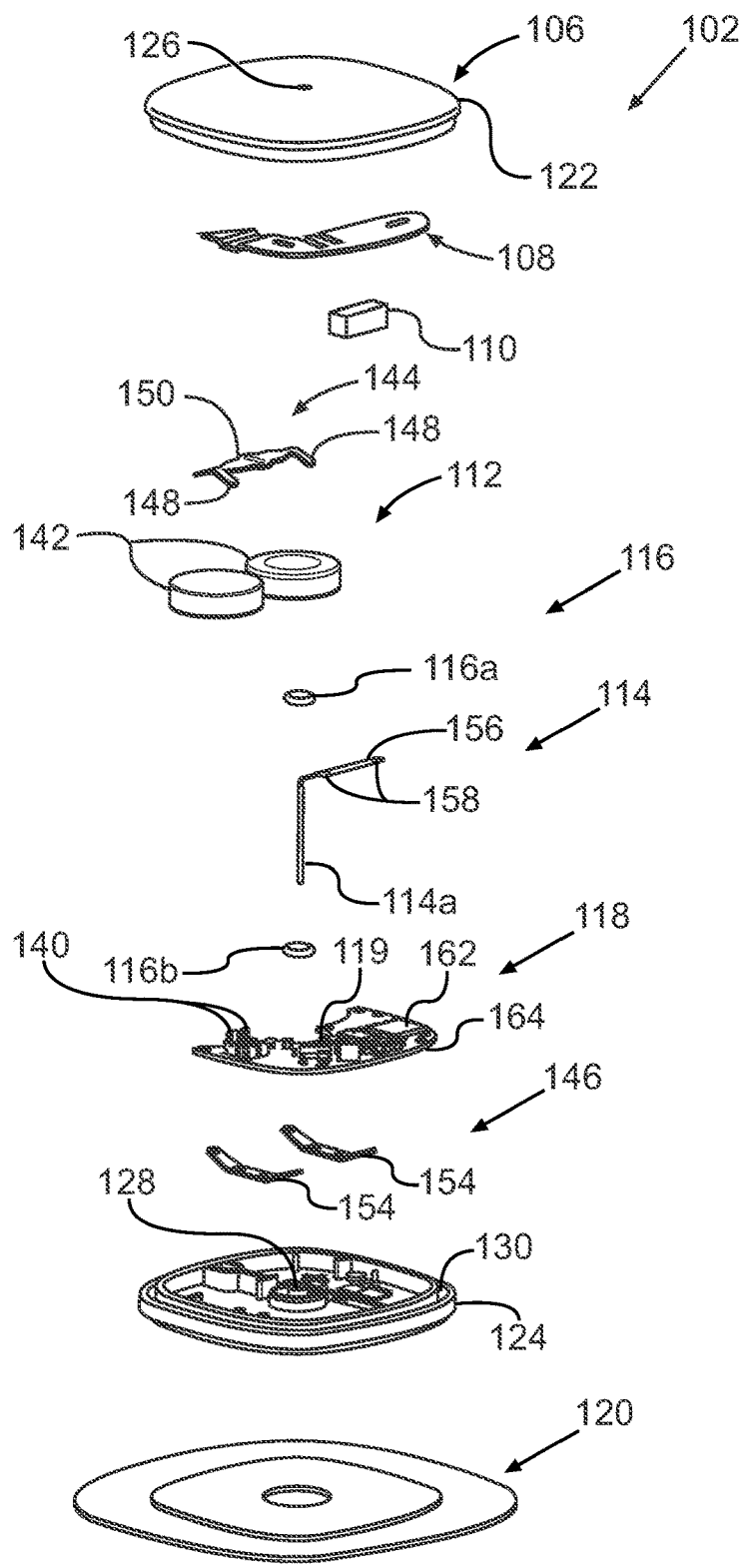
FIG. 3 is an exploded view of the physiological characteristic sensor of FIG. 1.

In one example, with reference to FIG. 3, the physiological characteristic sensor 102 includes a housing 106, an antenna 108, a sensor connector 110, a power source assembly 112, a glucose sensor 114, at least one sealing member 116, a printed circuit board assembly 118 and a coupling member or adhesive patch 120. The housing 106 is composed of a polymer-based material, and is molded, cast, formed via additively manufacturing, etc. In this example, the housing 106 is substantially rectangular, however, the housing 106 may have any desired shape that cooperates with the sensor inserter 104 to couple the physiological characteristic sensor 102 to the anatomy. The housing 106 has rounded corners to reduce snagging of the housing 106 on a user's clothing, for example. In one example, the housing 106 is a two-piece housing, which includes a first, top housing portion 122 and a second, bottom housing portion 124. The top housing portion 122 and the bottom housing portion 124 cooperate to enclose the antenna 108, the sensor connector 110, the power source assembly 112, a portion of the glucose sensor 114, the at least one sealing member 116, and the printed circuit board assembly 118. The top housing portion 122 includes a bore 126, which enables a portion of the sensor inserter 104 to pass through the housing 106 to couple the physiological characteristic sensor 102 to the anatomy. The bottom housing portion 124 includes a second bore 128, which cooperates with the bore 126 to enable the sensor inserter 104 and a portion of the glucose sensor 114 to pass through the housing 106. The bottom housing portion 124 may also include one or more dividers or compartments, to assist in containing the components of the physiological characteristic sensor 102. In addition, the bottom housing portion 124 may define a channel 130 about a perimeter of the bottom housing portion 124 to assist in coupling the top housing portion 122 to the bottom housing portion 124.

Figure 4:
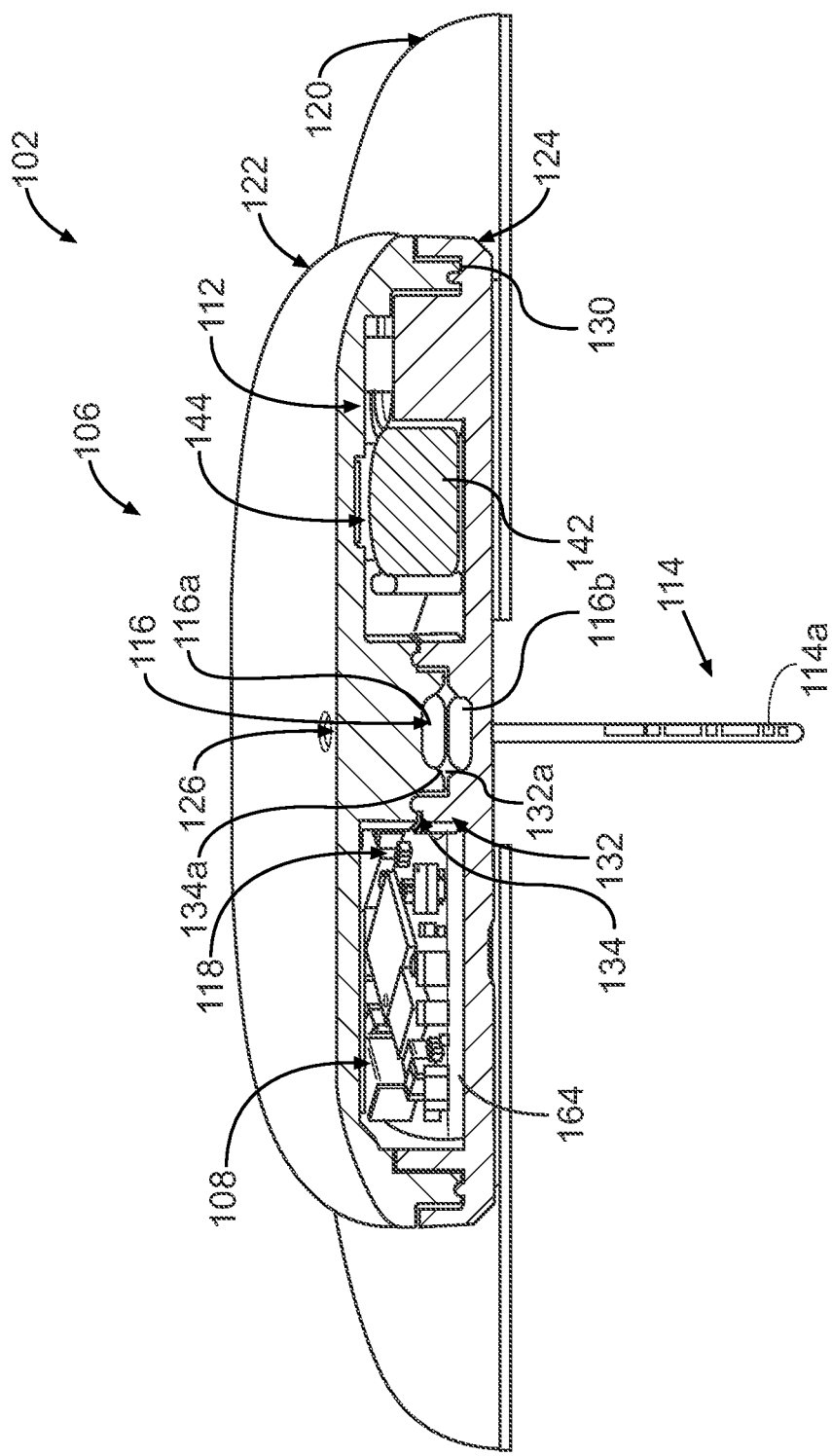
FIG. 4 is a cross-sectional view of the physiological characteristic sensor of FIG. 1, taken along line 4-4 of FIG. 2.

For example, with reference to FIG. 4, the top housing portion 122 is received within the channel 130. The top housing portion 122 is coupled to the bottom housing portion 124 within the channel 130, via welding, adhesives, etc. Generally, the top housing portion 122 is coupled to the bottom housing portion 124 to inhibit fluids, such as air, water, etc., from entering into the housing 106. In addition, in one example, the bottom housing portion 124 includes a cylindrical post 132, which is coupled to a mating cylindrical post 134 of the top housing portion 122 to couple the top housing portion 122 to the bottom housing portion 124 about the bore 126 and the second bore 128. The cylindrical post 132 also defines a first angled surface 132a, and the mating cylindrical post 134 also defines a second angled surface 134a. The first angled surface 132a is angled at upward from an inner perimeter of the cylindrical post 132 toward an outer perimeter of the cylindrical post 132. The second angled surface 134a is angled upward from an outer perimeter of the mating cylindrical post 134 toward the inner perimeter of the mating cylindrical post 134. Thus, with reference to FIG. 5, the angled surfaces 132a, 134a cooperate to define a diamond shaped cavity 136, which extends about a perimeter of the bore 126 and the second bore 128. The diamond shaped cavity 136 compresses the at least one sealing member 116 to form the seal about the glucose sensor 114, as will be discussed. In one example, the top housing portion 122 and the bottom housing portion 124 are coupled about a top surface of the cylindrical post 132 and the mating cylindrical post 134 to maintain a compression of the at least one sealing member 116.

With reference back to FIG. 6, the antenna 108 is coupled to the top housing portion 122. In this example, the antenna 108 is coupled to stakes 138 of the top housing portion 122 via heat stake, ultrasonic welding, etc. In one example, the antenna 108 is any suitable antenna 108 that enables bi-directional communication between the physiological characteristic sensor 102 and a portable electronic device of the user. Thus, generally, the antenna 108 enables wireless communication between the physiological characteristic sensor 102 and another device, including, but not limited to, an infusion pump, handheld device (tablet, smart phone, etc.) or other monitoring device. In one example, the antenna 108 may include, but is not limited to, a near field communication (NFC) antenna, RF radio antenna, a far field communication antenna, a wireless communication system configured to communicate via a wireless local area network (WLAN) using IEEE 802.11 standards or by using cellular data communication, a Bluetooth antenna, etc. In one example, the antenna 108 of the physiological characteristic sensor 102 is a Bluetooth low energy (BLE) antenna.

Figure 7:
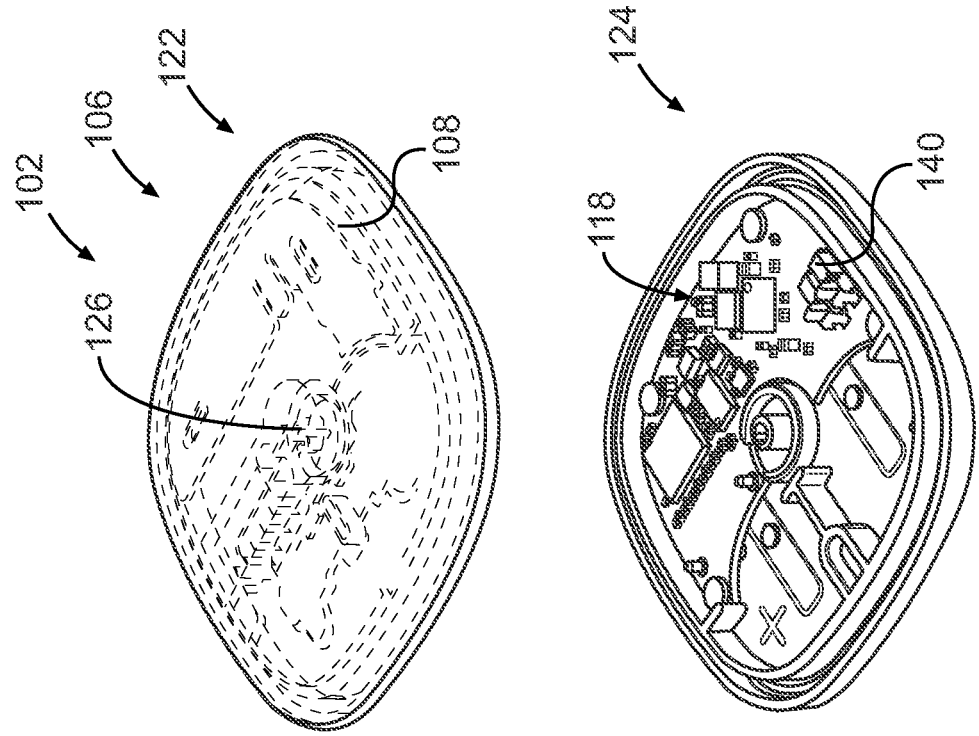
FIG. 7 is a partially exploded top perspective view of the physiological characteristic sensor, which illustrates an exemplary coupling for spring contacts associated with a printed circuit board assembly to a second housing portion of the housing of the physiological characteristic sensor.
Figure 7A:
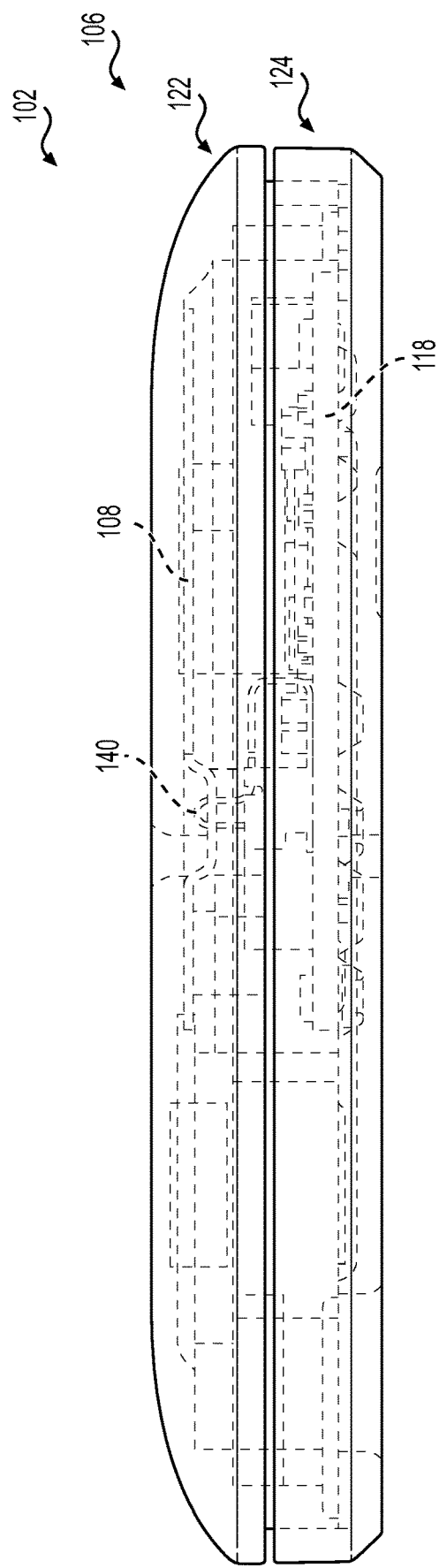
FIG. 7A is a side view of the physiological characteristic sensor, which illustrates the antenna of FIGS. 6 and 7 electrically coupled to the printed circuit board assembly.

In one example, with reference to FIG. 7, the antenna 108 is electrically coupled to and in communication with the printed circuit board assembly 118 via spring contacts 140. Thus, the antenna 108 is coupled to the printed circuit board assembly 118 without soldering, which reduces manufacturing complexity and time. In this example, the printed circuit board assembly 118 includes two spring contacts 140, however, the printed circuit board assembly 118 may have any suitable contact configuration to couple the antenna 108 to the printed circuit board assembly 118 upon assembly of the top housing portion 122 to the bottom housing portion 124. Thus, generally, with reference to FIG. 7A, the antenna 108 is coupled to the housing 106 such that the antenna 108 is electrically coupled to the printed circuit board assembly 118 upon assembly of the top housing portion 122 to the bottom housing portion 124 of the housing 106.

Figure 8:
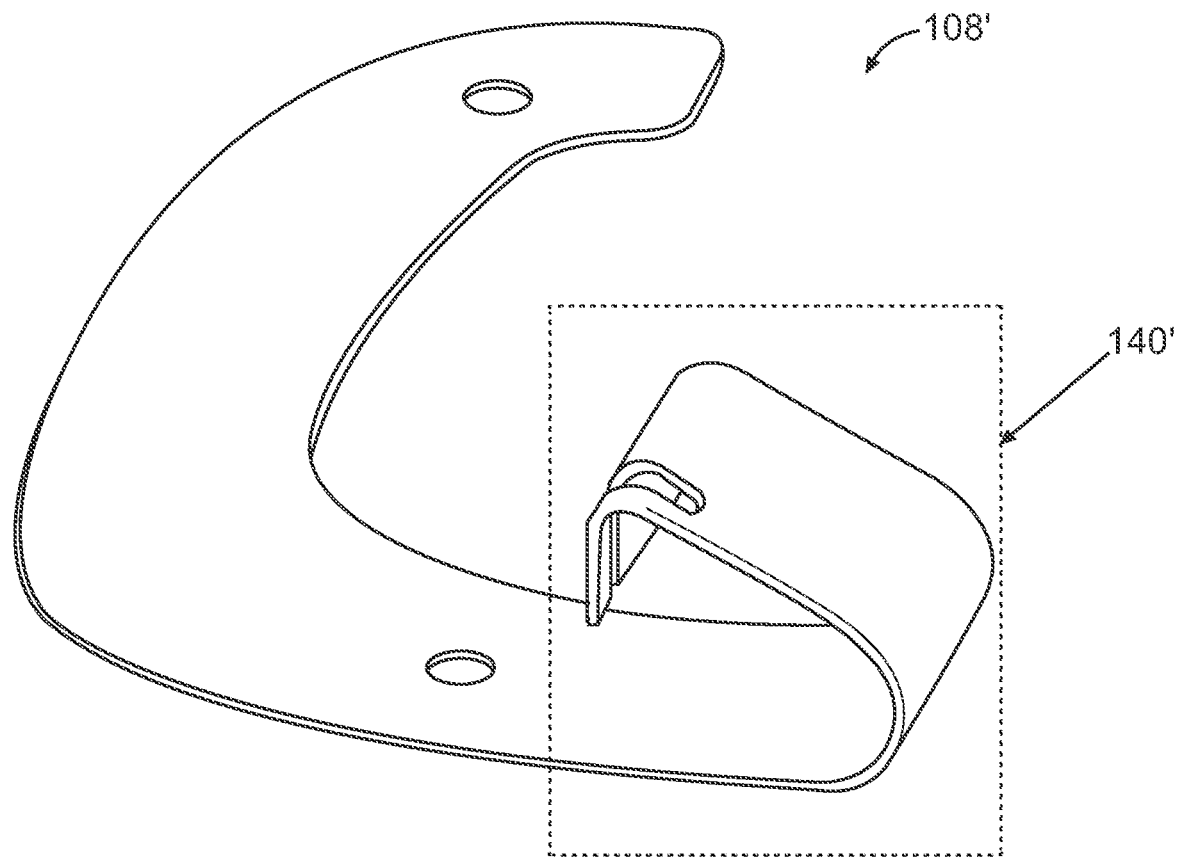
FIG. 8 is another exemplary antenna for use with the physiological characteristic sensor of FIG. 1.
Figure 9:
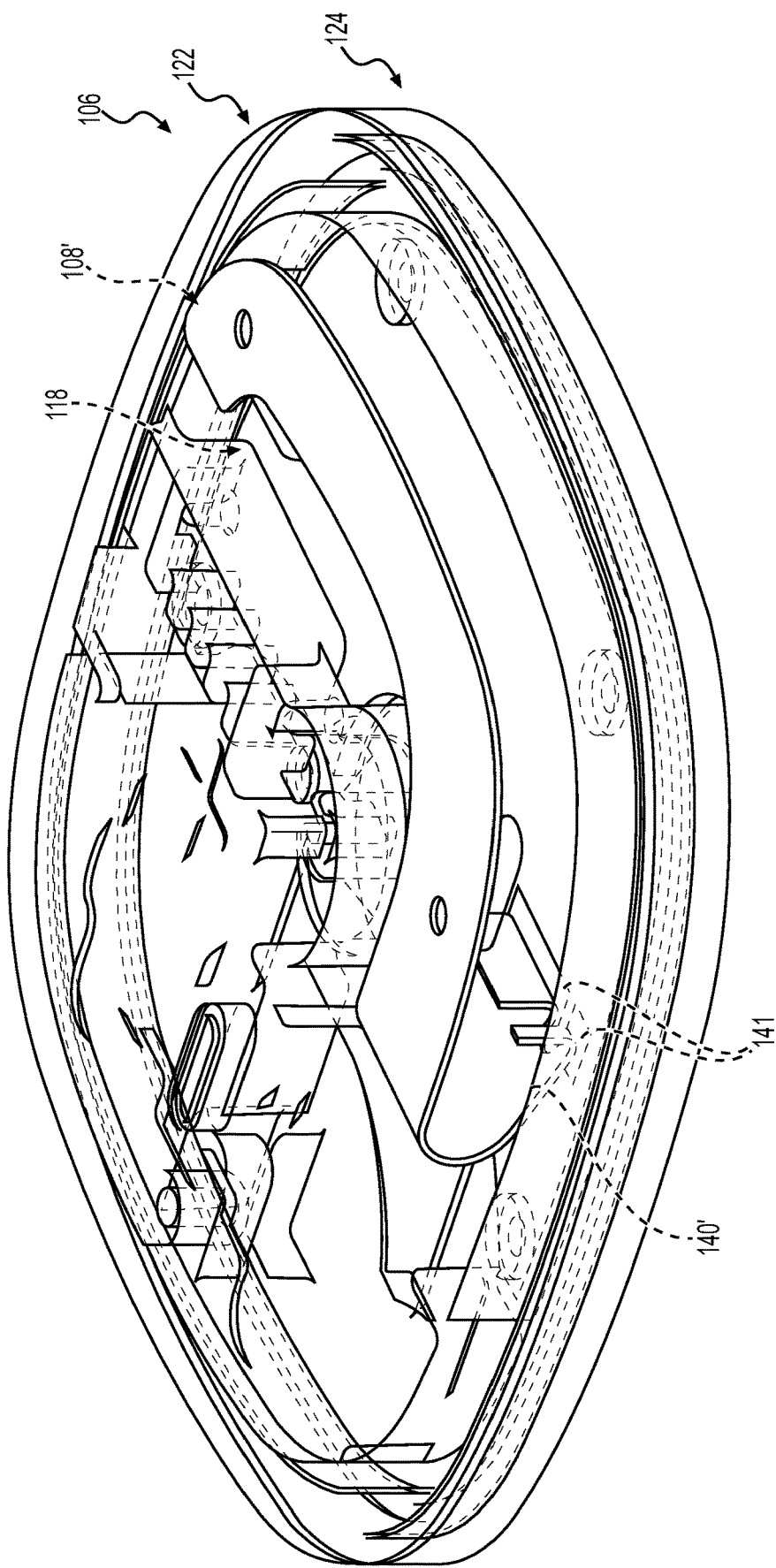
FIG. 9 is a perspective view of the antenna of FIG. 8 electrically coupled to the printed circuit board assembly of the physiological characteristic sensor.

Alternatively, with reference to FIG. 8, an antenna 108' is shown. The antenna 108' is substantially the same as the antenna 108, but the antenna 108' includes spring contacts 140'. The antenna 108' enables wireless communication between the physiological characteristic sensor 102 and another device, including, but not limited to, an infusion pump, handheld device (tablet, smart phone, etc.) or other monitoring device. In one example, the antenna 108 may include, but is not limited to, a near field communication (NFC) antenna, RF radio antenna, a far field communication antenna, a wireless communication system configured to communicate via a wireless local area network (WLAN) using IEEE 802.11 standards or by using cellular data communication, a Bluetooth antenna, etc. In one example, the antenna 108' of the physiological characteristic sensor 102 is a Bluetooth low energy (BLE) antenna. In this example, the spring contacts 140' are integrally formed with the antenna 108'. The spring contacts 140' are defined as a portion of the antenna 108', which is folded upon itself. With reference to FIG. 9, the spring contacts 140' touch contact pads 141 of the printed circuit board assembly 118 to electrically couple the antenna 108' to the printed circuit board assembly 118 such that the antenna 108' is in communication with the printed circuit board assembly 118. Thus, the antenna 108' is coupled to the printed circuit board assembly 118 without soldering, which reduces manufacturing complexity and time.

With reference back to FIG. 3, the sensor connector 110 provides a contact force between the glucose sensor 114 and the printed circuit board assembly 118. The sensor connector 110, in one example, is composed of a polymer-based material, and is cast, molded, additive manufactured, etc. When the top housing portion 122 is coupled to the bottom housing portion 124, the sensor connector 110 is held against the glucose sensor 114 by the top housing portion 122, which in turn, holds or maintains the glucose sensor 114 electrically coupled to the printed circuit board assembly 118.

The power source assembly 112 supplies power to the printed circuit board assembly 118. In one example, the power source assembly 112 includes at least one battery 142, a first, top contact or first battery contact 144 and a second, bottom contact or second battery contact 146. The at least one battery 142, in this example, comprises two batteries 142, each of which are coin-cell batteries. For example, the batteries 142 are each 1.55 volt (V) batteries. The first battery contact 144 and the second battery contact 146 are each composed of a metal or metal alloy, and may be stamped, cast, etc. The first battery contact 144 includes two spring tabs 148, which are interconnected by a body 150.

Figure 11:
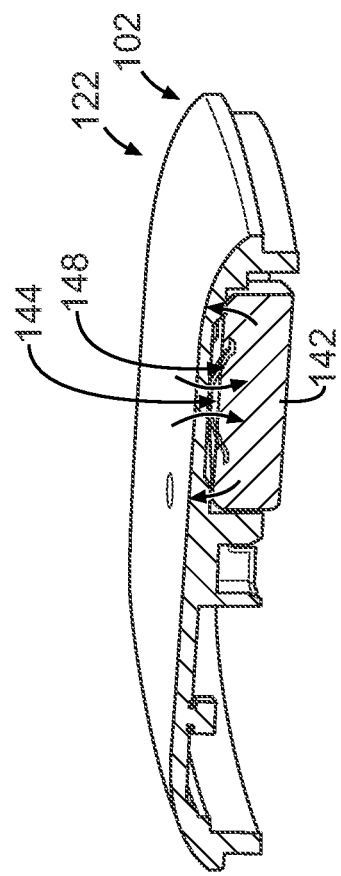
FIG. 11 is a schematic cross-sectional view, which illustrates a battery coupled to the first contact.
Figure 10:
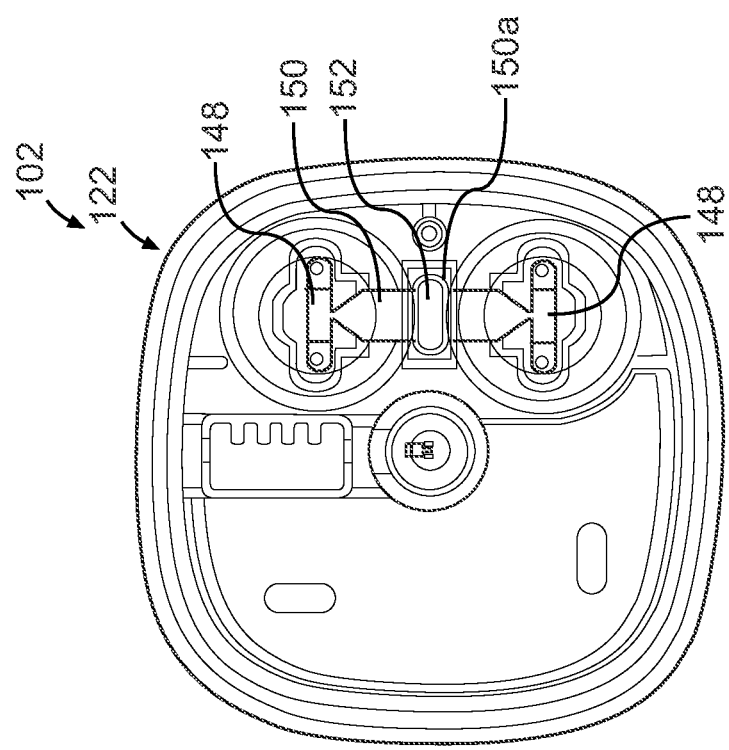
FIG. 10 is a bottom view of the first housing portion of the physiological characteristic sensor, which illustrates a first contact coupled to the first housing portion.

With reference to FIG. 10, the first battery contact 144 is shown coupled to the top housing portion 122. The first battery contact 144 is generally coupled to the top housing portion 122 via ultrasonic welding or heat stake welding with stake 152. The stake 152 is large to protect the first battery contact 144 during coupling of the top housing portion 122 to the bottom housing portion 124. The body 150 may define an opening 150a to receive the stake 152. The first battery contact 144 is generally coupled to the top housing portion 122 by the body 150 such that the spring tabs 148 are free to move relative to the body 150. By enabling the spring tabs 148 to move relative to the body 150, with reference to FIG. 11, the first battery contact 144 self-balances when moments are applied as the spring tabs 148 compress during coupling the top housing portion 122 to the bottom housing portion 124. This self-balancing of the first battery contact 144 via the spring tabs 148 minimizes damage to the first battery contact 144 during coupling of the top housing portion 122 to the bottom housing portion 124. In addition, by being movable, the spring tabs 148 limit a reaction force applied to the top housing portion 122 during use of the physiological characteristic sensor 102. With reference back to FIG. 3, the first battery contact 144 is symmetrical about a longitudinal axis of the first battery contact 144.

The second battery contact 146 comprises two second spring tabs 154, which are discrete from each other or not interconnected. The second spring tabs 154 are electrically and physically coupled to the printed circuit board assembly 118 such that when the top housing portion 122 is coupled to the bottom housing portion 124, the spring tabs 148 and 154 compress to electrically couple the batteries 142 together in series and to the printed circuit board assembly 118.

The glucose sensor 114 is an electrochemical sensor that includes the glucose oxidase enzyme, as is well understood by those familiar with glucose sensor technology. The glucose oxidase enzyme enables the glucose sensor 114 to monitor blood glucose levels in a diabetic patient or user by effecting a reaction of glucose and oxygen. Again, although certain embodiments pertain to glucose sensors, the technology described here can be adapted for use with any one of the wide variety of sensors known in the art. Generally, a distal end 114a of the glucose sensor 114 is cannulated and positionable in subcutaneous tissue of the user by an insertion needle of the sensor inserter 104 to measure the glucose oxidase enzyme.

Figure 13:
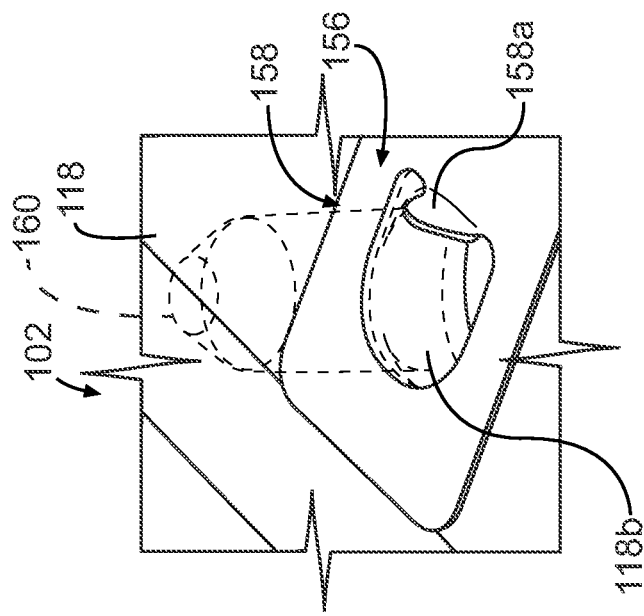
FIG. 13 is a detail view of one coupling post engaged with one coupling bore associated with the base of the glucose sensor taken at 13 of FIG. 12.

In one example, the glucose sensor 114 includes a base 156 that is coupled to the distal end 114a of the glucose sensor 114 at about a ninety degree angle. The base 156 couples the glucose sensor 114 to the printed circuit board assembly 118. In this example, the base 156 includes two coupling bores 158. The coupling bores 158 are spaced apart on the base 156 and couple or anchor the glucose sensor 114 on the printed circuit board assembly 118. In one example, with reference to FIG. 12, the base 156 is shown coupled to the printed circuit board assembly 118 via the coupling bores 158. In this example, the bottom housing portion 124 includes coupling posts 160, which extend through bores 118b defined in the printed circuit board assembly 118 to mate respectively with the coupling bores 158. Each of the coupling bores 158 include a coupling tab 158a. With reference to FIG. 13, the coupling tab 158a is bendable upon placement of the respective coupling bore 158 over the respective coupling post 160 to securely couple the base 156, and thus, the glucose sensor 114 to the bottom housing portion 124. The coupling of the base 156 to the coupling posts 160, in turn, also electrically and mechanically couples the glucose sensor 114 to the printed circuit board assembly 118. The coupling tab 158a extends into the coupling bore 158 such that the bending of the coupling tab 158a by the coupling post 160 creates an interference fit between the coupling tab 158a and the coupling post 160 to retain the glucose sensor 114 on the printed circuit board assembly 118. The interference fit between the coupling bores 158 and the coupling posts 160 also inhibits a sliding movement of the glucose sensor 114 relative to the printed circuit board assembly 118.

Figure 5:
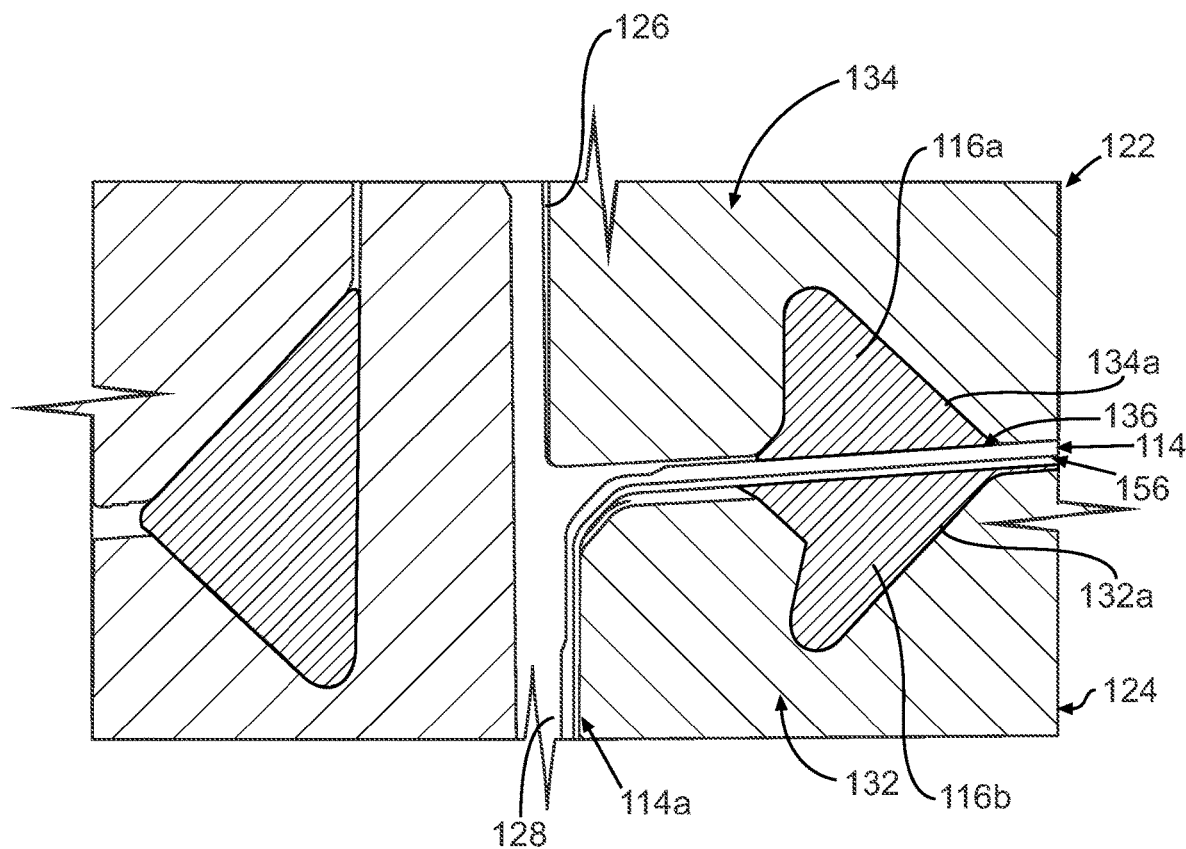
FIG. 5 is a detail view of a seal formed by at least one sealing member about a distal end of a glucose sensor associated with the physiological characteristic sensor of FIG. 1.

With reference back to FIG. 3, the at least one sealing member 116 includes two sealing members 116a, 116b. The sealing members 116a, 116b comprise O-rings, which are composed of an elastomeric material. With reference to FIG. 5, the sealing members 116a, 116b are positioned on either side of the base 156 of the glucose sensor 114 and surround the distal end 114a to waterproof or inhibit fluids from entering into the housing 106. The assembly of the top housing portion 122 to the bottom housing portion 124 causes the angled surfaces 132a, 134a to contact and compress the sealing members 116a, 116b, which causes the sealing members 116a, 116b to deform and fill the space surrounding the distal end 114a. The deformation of the sealing members 116a, 116b by the top housing portion 122 seals about the distal end 114a of the glucose sensor 114, and inhibits fluids from entering into the housing 106. Thus, the deformation of the sealing members 116a, 116b forms a seal between the top housing portion 122 and the bottom housing portion 124 about the distal end 114a of the glucose sensor 114. The seal formed between the top housing portion 122 and the distal end 114a by the sealing member 116a and the seal formed between the bottom housing portion 124 and the distal end 114a by the sealing member 116b is formed without requiring adhesives, grease or other components to ensure a waterproof seal, which reduces manufacturing complexity.

With reference to FIG. 3, the printed circuit board assembly 118 includes a controller or control module 162. The control module 162 includes at least one processor and a computer readable storage device or media, which are mounted to a printed circuit board 164. The printed circuit board 164 is electrically and mechanically coupled to the spring contacts 140, and electrically couples the batteries 142, the glucose sensor 114 and the antenna 108 to the control module 162. Thus, the batteries 142, the glucose sensor 114 and the antenna 108 are in communication with the control module 162. The processor can be any custom made or commercially available processor, a central processing unit (CPU), an auxiliary processor among several processors associated with the control module 162, a semiconductor based microprocessor (in the form of a microchip or chip set), a macroprocessor, any combination thereof, or generally any device for executing instructions. The computer readable storage device or media may include volatile and nonvolatile storage in read-only memory (ROM), random-access memory (RAM), and keep-alive memory (KAM), for example. KAM is a persistent or non-volatile memory that may be used to store various operating variables while the processor is powered down. The computer-readable storage device or media may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the control module 162 in controlling components associated with the physiological characteristic sensor 102.

The instructions may include one or more separate programs, each of which comprises an ordered listing of executable instructions for implementing logical functions. The instructions, when executed by the processor, receive and process input signals, perform logic, calculations, methods and/or algorithms for controlling the components of the physiological characteristic sensor 102, and generate signals to components of the physiological characteristic sensor 102 to monitor the glucose sensor 114 and control the antenna 108 based on the logic, calculations, methods, and/or algorithms Although only one control module 162 is shown, embodiments of the physiological characteristic sensor 102 can include any number of control modules that communicate over any suitable communication medium or a combination of communication mediums and that cooperate to process the signals from the glucose sensor 114, transmit signals received from the glucose sensor 114 via the antenna 108, perform logic, calculations, methods, and/or algorithms, and generate control signals to control features of the physiological characteristic sensor 102.

In various embodiments, one or more instructions of the control module 162, when executed by the processor, receive and process signals from the glucose sensor 114 to determine a blood glucose level of the user. The one or more instructions of the control module 162, when executed by the processor, also communicate the blood glucose level via the antenna 108 to the portable electronic device associated with the user.

The printed circuit board assembly 118 also includes a magnet sensor 119. The magnet sensor 119 observes a magnetic field, including, but not limited to a magnetic field generated by a magnet 214 associated with the sensor inserter 104 (FIG. 14), and generates one or more sensor signals based on the observation of the magnetic field. In one example, the processor receives the sensor signals from the magnet sensor 119 and initiates the physiological characteristic sensor 102 for the monitoring of the blood glucose levels. Stated another way, based on the observation of a change in a magnetic field, such as due to a separation of the magnet 214 from the physiological characteristic sensor 102, the physiological characteristic sensor 102 is activated to monitor the blood glucose levels. The magnet sensor 119 is electrically and mechanically coupled to the printed circuit board 164, and is in communication with the control module 162. In one example, the magnet sensor 119 is a tunneling magnetoresistive (TMR) sensor. The use of the magnet sensor 119 in cooperation with the magnet 214 maintains the physiological characteristic sensor 102 in a low-power state in the presence of the magnetic field generated by the magnet 214, which preserves a life of the batteries 142 prior to the deployment of the physiological characteristic sensor 102 (i.e. when the physiological characteristic sensor 102 is on the shelf).

The adhesive patch 120 is coupled to the bottom housing portion 124 and affixes the bottom housing portion 124, and thus, the glucose sensor 114, to an anatomy, such as the skin of the user. The adhesive patch 120 may be composed of a flexible and breathable material with one or more adhesive layers, such as cloth, a bandage-like material, and the like. For example, suitable materials could include polyurethane, polyethylene, polyester, polypropylene, polytetrafluoroethylene (PTFE), or other polymers, to which one or more adhesive layers are applied. The adhesive patch 120 may be coupled to the bottom housing portion 124 via adhesives, ultrasonic welding, etc.

Figure 12:
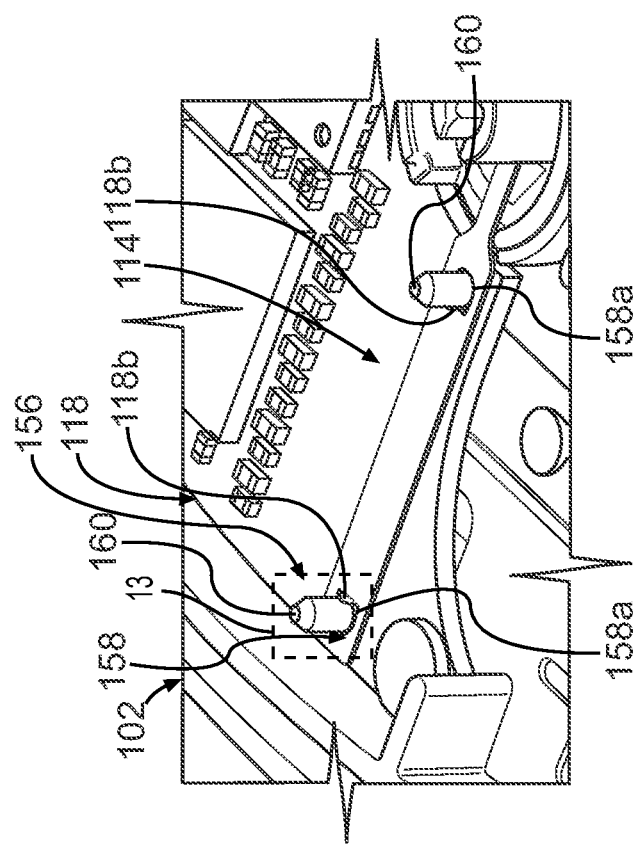
FIG. 12 is a detail view of a base of a glucose sensor associated with the physiological characteristic sensor of FIG. 1 coupled to the printed circuit board assembly.

In one example, in order to assemble the physiological characteristic sensor 102, with the bottom housing portion 124 formed, the second battery contact 146 is coupled to the bottom housing portion 124. With the control module 162 and the spring contacts 140 coupled to the printed circuit board 164, the printed circuit board 164 is coupled to the bottom housing portion 124 such that the coupling posts 160 pass through the bores 118b (FIG. 12). The sealing member 116b is coupled to the bottom housing portion 124 adjacent to the cylindrical post 132. With brief reference to FIG. 12, the glucose sensor 114 is coupled to the bottom housing portion 124 by aligning the coupling bores 158 with the coupling posts 160. The base 156 is advanced toward the printed circuit board assembly 118, which causes the coupling tabs 158a to bend. The bending of the coupling tabs 158a retains the glucose sensor 114 on the bottom housing portion 124 and electrically coupled to the printed circuit board assembly 118. With reference to FIG. 4, the distal end 114a of the glucose sensor 114 extends through the sealing member 116b and through the second bore 128. The batteries 142 are positioned within the bottom housing portion 124 so as to be coupled to the second battery contact 146.

Figure 6:
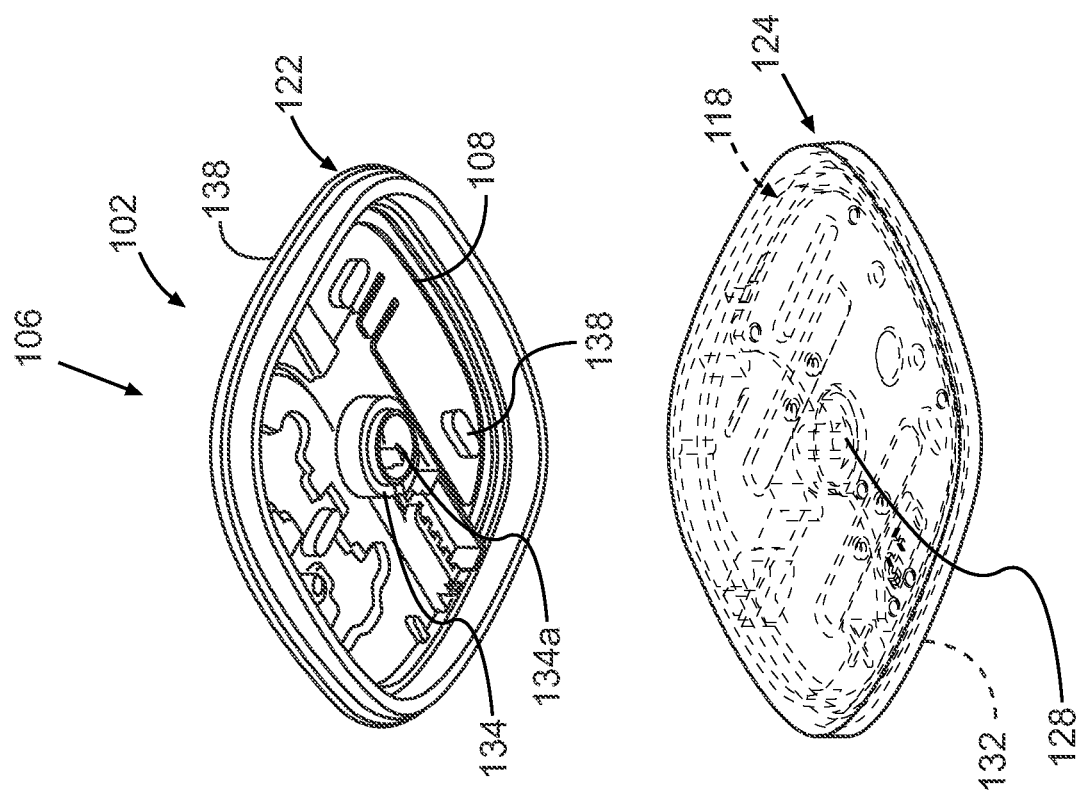
FIG. 6 is a partially exploded bottom perspective view of the physiological characteristic sensor, which illustrates an exemplary coupling for an antenna to a first housing portion of a housing of the physiological characteristic sensor.

With reference back to FIG. 3, with the top housing portion 122 formed, the first battery contact 144 is coupled to the top housing portion 122 at the body 150 (FIG. 10). The antenna 108, 108' is coupled to the top housing portion 122 (FIG. 6). The sealing member 116a is positioned opposite the sealing member 116b. The top housing portion 122 is coupled to the bottom housing portion 124 such that the top housing portion 122 is received within the channel 130. The coupling of the top housing portion 122 to the bottom housing portion 124 causes the angled surfaces 132a, 134a to compress the sealing members 116a, 116b to form the seal about the distal end 114a of the glucose sensor 114. The coupling of the top housing portion 122 to the bottom housing portion 124 also causes the spring tabs 148 (FIG. 3) of the first battery contact 144 to electrically couple the batteries 142 together in series. In addition, the coupling of the top housing portion 122 to the bottom housing portion 124 electrically couples the antenna 108 to the spring contacts 140 of the printed circuit board assembly 118. Generally, the physiological characteristic sensor 102 provides for reduced assembly time and improved manufacturability.

With reference back to FIG. 2, in various embodiments, the physiological characteristic sensor 102 is coupled to the sensor inserter 104 for shipping and delivering the physiological characteristic sensor 102 to the user. The sensor inserter 104 is manipulatable by a user to couple the glucose sensor 114 and the physiological characteristic sensor 102 to the user. With additional reference to FIG. 14, the sensor inserter 104 includes a needle inserter 198, a plunger 200, a first biasing member or insertion spring 202, a needle retractor 204, a second biasing member or retraction spring 206, a frame 208, a sensor retainer 210, a sensor carrier 212, the magnet 214 and a cap 216. In this example, the cap 216 includes a membrane 218, as will be discussed further herein.

Figure 16:
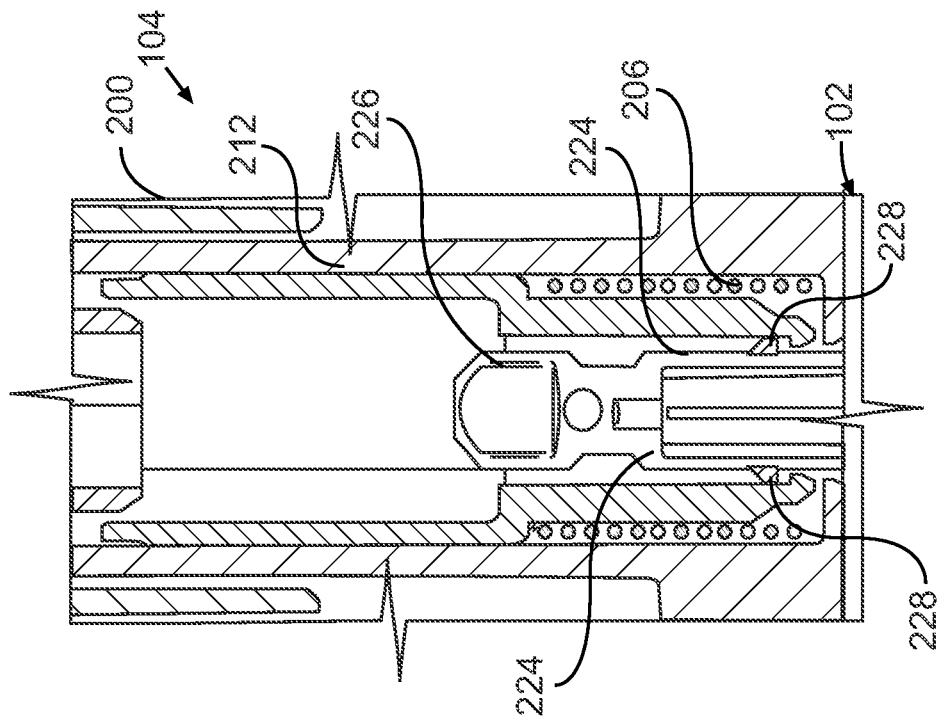
FIG. 16 is a detail view of the needle inserter coupled to a needle retractor of the sensor inserter of FIG. 1.
Figure 15:
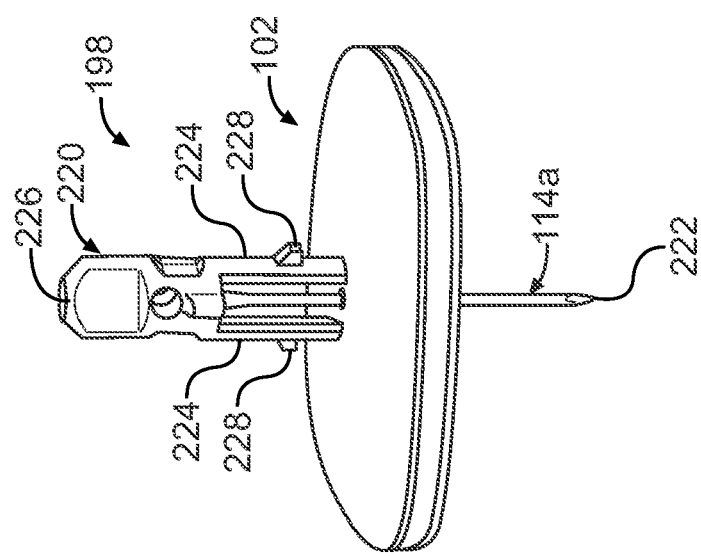
FIG. 15 is a perspective view of a needle inserter of the sensor inserter coupled to the physiological characteristic sensor of FIG. 1.

The needle inserter 198 is composed of a polymer-based material, and is cast, molded, additive manufactured, etc. With reference to FIG. 15, the needle inserter 198 is shown coupled to the physiological characteristic sensor 102. Generally, the needle inserter 198 is coupled to the physiological characteristic sensor 102 prior to coupling the physiological characteristic sensor 102 to the sensor inserter 104, which provides ease of assembly. The needle inserter 198 includes a carrier 220 and an insertion needle 222. The carrier 220 is overmolded onto the insertion needle 222. The carrier 220 includes a pair of arms 224. Each of the arms 224 extend from either side of a carrier base 226. The carrier base 226 provides a graspable portion for coupling the needle inserter 198 to the physiological characteristic sensor 102. The arms 224 each include an arm tab 228. With reference to FIG. 16, the arm tabs 228 are coupled to and engage with a lip 230 of the needle retractor 204. As will be discussed, the engagement between the arm tabs 228 and the lip 230 enables the needle retractor 204 to remove the insertion needle 222 from the anatomy. With reference back to FIG. 15, the insertion needle 222 is generally a stainless steel needle, which extends for a distance beyond the distal end 114a of the glucose sensor 114 to couple the glucose sensor 114 to the anatomy.

With reference back to FIG. 14, the plunger 200 is composed of a biocompatible polymer, and may be molded, cast, printed, etc. The plunger 200 surrounds the frame 208, and includes a plurality of threads 236 defined about a surface of the outer housing 600 adjacent to a second, bottom end 200b. The threads 236 removably couple the cap 216 to the plunger 200, as will be discussed. The plunger 200 is shaped to correspond to the shape of the physiological characteristic sensor 102 so that the user intuitively knows the position and orientation of the physiological characteristic sensor 102 when the sensor inserter 104 is used to couple the physiological characteristic sensor 102 to the anatomy. This enables the user to position the sensor inserter 104 at a location by feel, without having to see the insertion site, such as a back of an arm, for example. In one example, a first, top end 200a of the plunger 200 includes a recess or dimple that is coaxial with the insertion needle 222 to enable the user to visualize the location of the distal end 114a within the anatomy.

With reference back to FIG. 2, the plunger 200 also defines a first inner guide surface 238 and a second inner guide surface 240. Each of the first inner guide surface 238 and the second inner guide surface 240 extend radially inward from an inner surface of the plunger 200. In this example, each of the first inner guide surface 238 and the second inner guide surface 240 extend from the first, top end 200a toward the bottom end 200b. In one example, the first inner guide surface 238 includes a slot that cooperates with a rail 242 defined within the needle retractor 204. The engagement of the rail 242 with the slot guides the needle retractor 204 toward the top end 200a of the plunger 200 to ensure the insertion needle 222 associated with the needle inserter 198 that is coupled to the needle retractor 204 is retained within the plunger 200 after deployment of the physiological characteristic sensor 102. The second inner guide surface 240 cooperates with the sensor carrier 212 to guide the sensor carrier 212 during deployment of the physiological characteristic sensor 102. The plunger 200 also includes a plurality of projections 244 that extend radially inward spaced apart about an interior periphery of the plunger 200. The projections 244 cooperate with slots 246 defined in the frame 208. Generally, the projections 244 and the slots 246 cooperate to a guide a movement of the plunger 200 relative to the frame 208. The plunger 200 also includes frame projections 247. The frame projections 247 extend radially inward and are defined about a perimeter of the plunger 200. As will be discussed, the frame projections 247 cooperate with the frame 208 to release the physiological characteristic sensor 102 when the sensor inserter 104 is in a second position.

The insertion spring 202 is a helical coil spring, which is composed of a suitable biocompatible material, such as a spring steel that is wound to form the insertion spring 202. In one example, the insertion spring 202 is a tension spring, which is received between the second inner guide surface 240 of the plunger 200 and a surface 212a of the sensor carrier 212. Generally, the insertion spring 202 expands as the sensor carrier 212 moves toward a second, bottom end 208b of the frame 208 to couple the physiological characteristic sensor 102 to the user and exerts a spring force F1 along a longitudinal axis L to move the sensor carrier 212 toward the bottom end 208b of the frame 208 for deployment of the physiological characteristic sensor 102.

Figure 14:
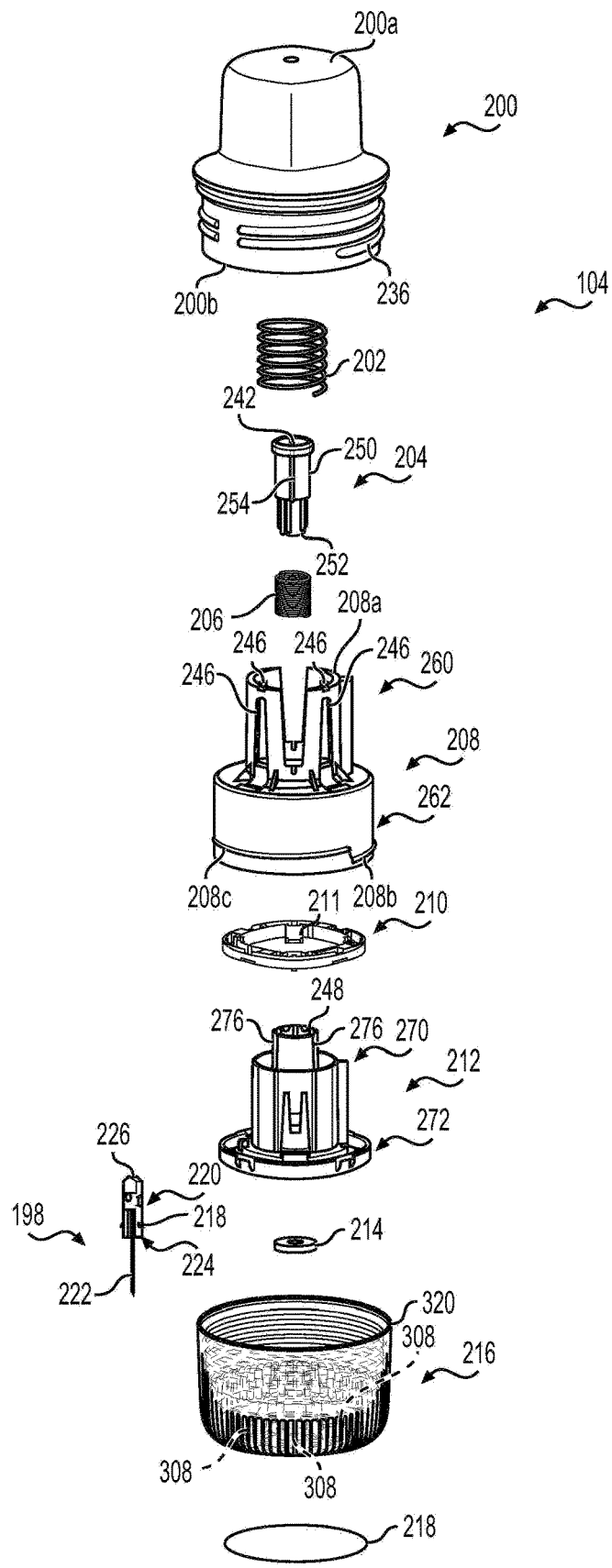
FIG. 14 is an exploded view of the sensor inserter of FIG. 1.

The needle retractor 204 is coupled to a second annular projection 248 of the sensor carrier 212. With reference to FIG. 14, the needle retractor 204 includes a first portion 250 and a second portion 252. The first portion 250 has a greater diameter than the second portion 252. The first portion 250 includes one or more guide projections 254, which are spaced apart about a perimeter of the first portion 250. The guide projections 254 contact the second annular projection 248. The second portion 252 is coupled to the needle inserter 198. The diameter of the second portion 252 is sized such that the retraction spring 206 is positioned between the first portion 250 and the sensor carrier 212 so as to surround the second portion 252, as shown in FIG. 2.

Figure 2:
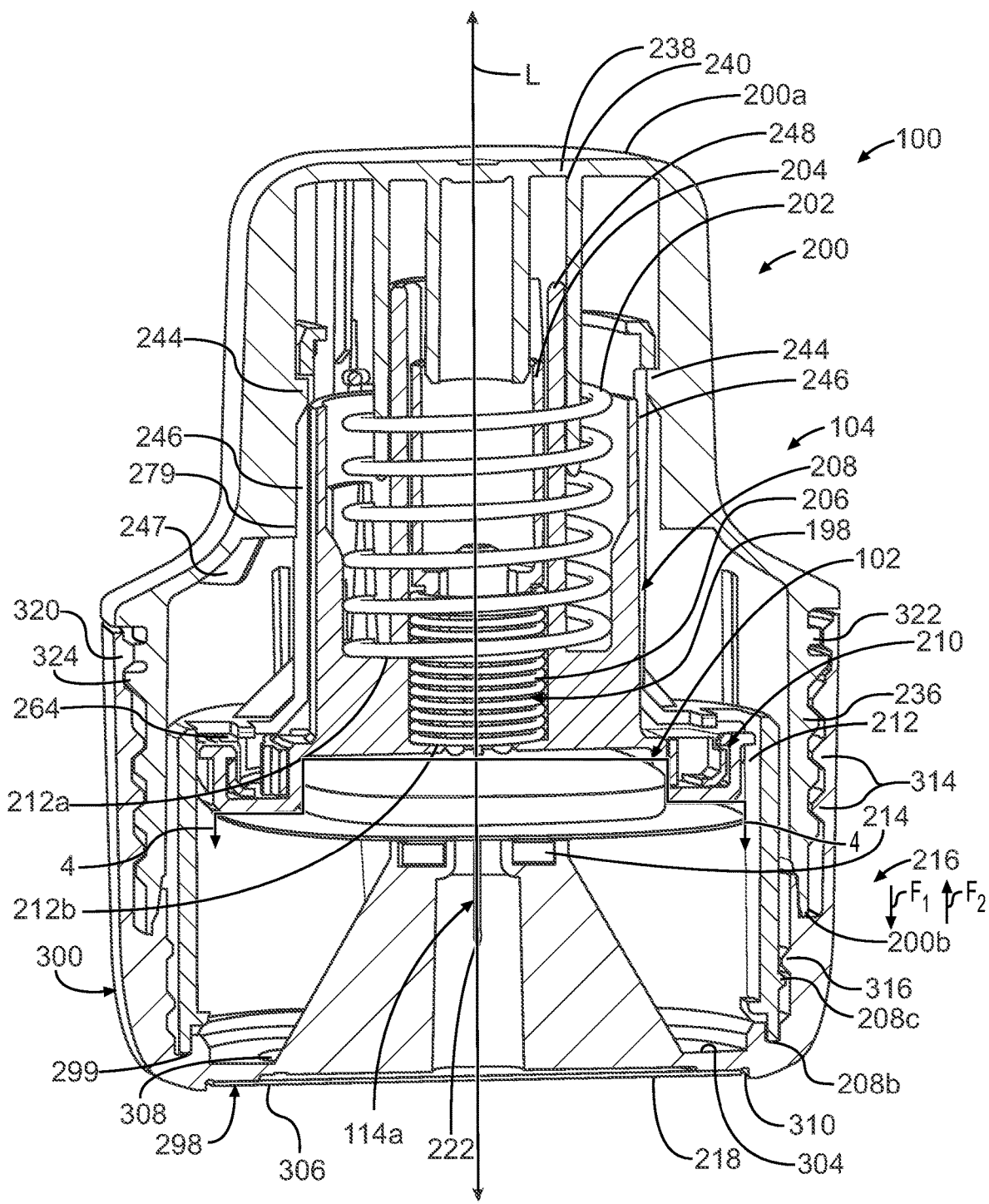
FIG. 2 is a cross-sectional view of the physiological characteristic sensor system of FIG. 1, taken along line 2-2 of FIG. 1.

With continued reference to FIG. 2, the retraction spring 206 is a helical coil spring, which is composed of a suitable biocompatible material, such as a spring steel that is wound to form the retraction spring 206. In one example, the retraction spring 206 is a compression spring, which is received between the second portion 252 of the needle retractor 204 and a surface 212b of the sensor carrier 212. After deployment, the retraction spring 206 expands and exerts a spring force F2 along the longitudinal axis L to move the needle retractor 204 toward the first inner guide surface 238 of the plunger 200 to retain the insertion needle 222 within the sensor inserter 104.

The frame 208 is received within the plunger 200. Generally, the frame 208 extends a distance beyond the plunger 200 when the physiological characteristic sensor 102 is coupled to the sensor inserter 104. The frame 208 is composed of a biocompatible polymer, and may be molded, cast, printed, etc. With reference to FIG. 14, the frame 208 includes a first frame portion 260 and a second frame portion 262. The slots 246 are defined in the first frame portion 260 and extend from a top surface 208a of the frame 208 to the second frame portion 262. The second frame portion 262 surrounds the sensor carrier 212 such that the physiological characteristic sensor 102 is positioned within the second frame portion 262 of the frame 208. In one example, with reference to FIG. 17, the second frame portion 262 includes at least one or a plurality of ribs 264. FIG. 17 is an end view of the physiological characteristic sensor 102 coupled to the sensor retainer 210, and the sensor retainer 210 is coupled to the frame 208. As shown, the ribs 264 are spaced apart about the inner perimeter of the frame 208, and extend for a distance to engage with the sensor retainer 210. As will be discussed, in a first position, the ribs 264 engage with the sensor retainer 210 to retain the physiological characteristic sensor 102. In the second position, the ribs 264 are released, via contact between the frame projections 247 of the plunger 200 and the ribs 264, which causes the sensor retainer 210 to release the physiological characteristic sensor 102 for deployment onto the anatomy.

The sensor retainer 210 is coupled to and received about a perimeter of the sensor carrier 212. In one example, the sensor retainer 210 assists in coupling or retaining the physiological characteristic sensor 102 on the sensor carrier 212. The sensor retainer 210 defines a central bore 211 that receives the physiological characteristic sensor 102 (FIGS. 14 and 18). The sensor retainer 210 may be composed of a biocompatible polymer, and may be molded, cast, printed, etc. With reference to FIG. 17, the sensor retainer 210 includes at least one or plurality of retainer arms 266, which are spaced apart about a perimeter of the sensor retainer 210 and are spaced apart about the central bore 211. In FIG. 17, the sensor retainer 210 is shown with the retainer arms 266 in a first, fired or released state. Each of the retainer arms 266 is cantilevered from the sensor retainer 210, and includes a contact surface 268 that retains the physiological characteristic sensor 102 in a second, pre-fired or coupled state. In the first state, the contact surface 268 of the retainer arms 266 do not contact the physiological characteristic sensor 102 such that the physiological characteristic sensor 102 is released or uncoupled from the sensor retainer 210 when the retainer arms 266 are in the first state. In the first state, a gap 269 is defined between a terminal end 266a of each of the retainer arms 266 and a surface 210b of the sensor retainer 210.

With reference to FIG. 18, in the second state, each of the ribs 264 of the frame 208 contact a respective one of the retainer arms 266 to bias or compress the retainer arms 266 into the second state. In the second state, the gap 269 is substantially eliminated and the terminal end 266a of each of the retainer arms 266 contacts a surface 210b of the sensor retainer 210. In the second state, as also shown in FIG. 19, the contact surface 268 is held against the physiological characteristic sensor 102 to retain the physiological characteristic sensor 102 on the sensor retainer 210. As shown in FIG. 19, the contact surface 268 is substantially L-shaped, and at least partially contacts a surface 124a of the bottom housing portion 124 of the physiological characteristic sensor 102.

Figure 21:
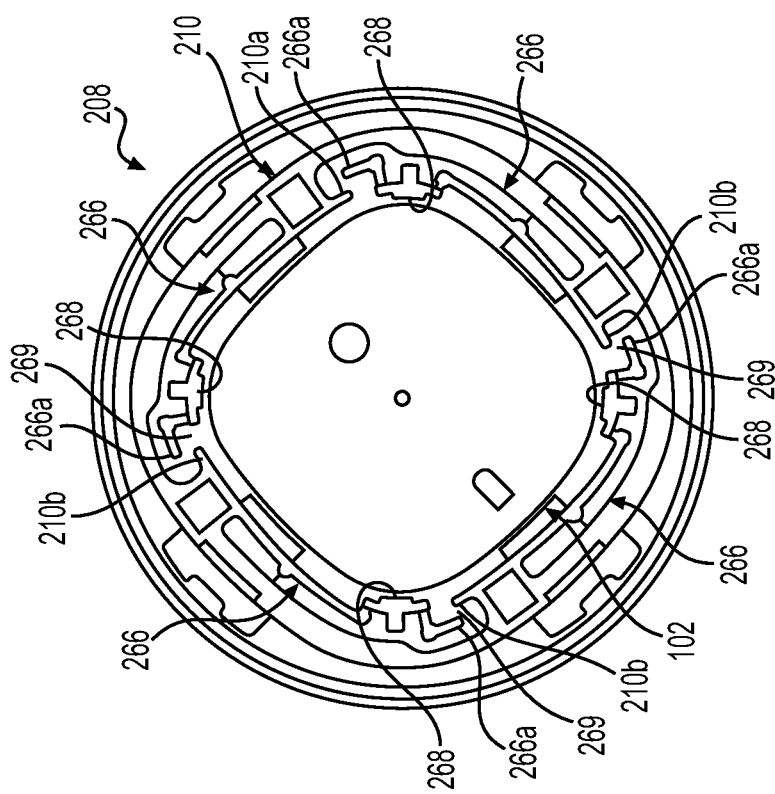
FIG. 21 is a bottom view of the sensor carrier of FIG. 17, which illustrates the at least one retainer arm of the sensor retainer uncoupled from the physiological characteristic sensor in the first state.
Figure 20:
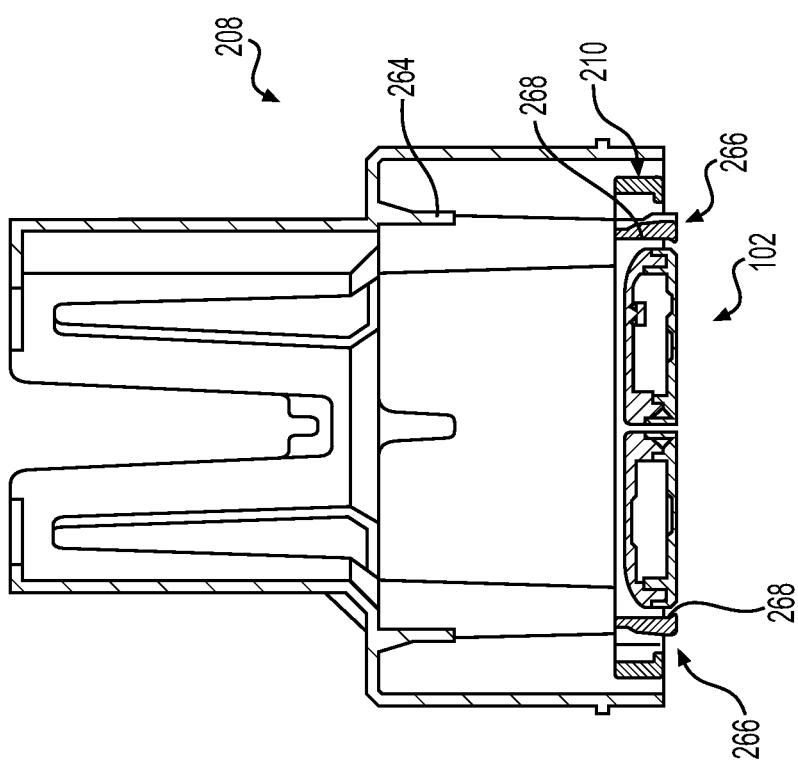
FIG. 20 is a perspective view of the sensor retainer coupled to the frame associated with the sensor inserter of FIG. 1, which illustrates the at least one rib of the frame releasing the at least one retainer arm such that the at least one retainer arm is in the first state.

With reference to FIG. 20, the sensor retainer 210 is shown released from the frame 208 to deploy the physiological characteristic sensor 102 on the anatomy. The frame projections 247 of the plunger 200 contact the ribs 264 of the frame 208, which pushes the ribs 264 outward, thereby releasing the retainer arms 266. The release of the retainer arms 266 moves the retainer arms 266 from the second state to the first state, as shown in FIG. 21. In FIG. 21, the retainer arms 266 have moved to the first state, which releases the contact surface 268 from the physiological characteristic sensor 102. By the retainer arms 266 moving to the first state from the second state, the user is able to separate the physiological characteristic sensor 102 from the sensor inserter 104 with little to zero force and without disturbing the insertion site.

With reference back to FIG. 14, the sensor carrier 212 moves relative to the frame 208 to deploy the physiological characteristic sensor 102 onto the user. The sensor carrier 212 may be composed of a biocompatible polymer, and may be molded, cast, printed, etc. The sensor carrier 212 includes a support body 270 and a retaining flange 272. With reference to FIG. 22, the support body 270 is annular, and includes a first annular projection 274 and the second annular projection 248 that are concentric. The first annular projection 274 couples the sensor carrier 212 to the frame 208, and the second annular projection 248 couples the needle retractor 204 to the sensor carrier 212. The second annular projection 248 may also include opposed slots 276, which cooperate with the needle retractor 204 to couple the needle retractor 204 to the sensor carrier 212. With reference to FIG. 23, the sensor carrier 212 also includes insertion snaps 278. The insertion snaps 278 extend outwardly from the first annular projection 274, and are received within the slots 246 of the frame 208. As shown in FIG. 23, in the first position, the insertion snaps 278 are spaced apart from a surface 246a of the slots 246 to inhibit a relative movement between the sensor carrier 212 and the frame 208. As will be discussed, with reference to FIG. 24, the cap 216 applies a force F3 to the physiological characteristic sensor 102 in the first position, which causes the insertion snaps 278 of the sensor carrier 212 to be spaced apart from the surface 246a of the frame 208 (FIG. 23) and free floating. With reference back to FIG. 23, a space 280 defined between the insertion snaps 278 and the surface 246a ensures that if the sensor inserter 104 is accidentally mishandled in the first position, the sensor carrier 212 is not inadvertently released. Stated another way, the space 280 ensures that the sensor inserter 104 remains in the first position until the user pushes on the plunger 200 and inhibits an accidental movement of the sensor inserter 104 from the first position to the second position.

With brief reference to FIG. 2, a ramp surface 279 defined interiorly within the plunger 200 contacts the insertion snaps 278 as the plunger 200 moves relative to the frame 208. The contact between the ramp surface 279 and the insertion snaps 278 causes the insertion snaps 278 (FIG. 23) to deflect, thereby releasing the insertion snaps 278 (FIG. 23) from the slots 246 (FIG. 23) and from the frame 208. The release of the sensor carrier 212 from the frame 208 enables the insertion spring 202 to apply the force F1 to couple the physiological characteristic sensor 102 to the anatomy.

Figure 26:
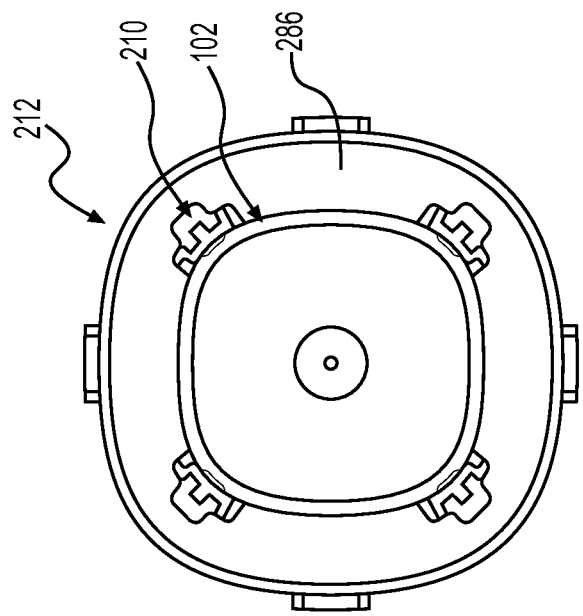
FIG. 26 is a bottom view of the sensor carrier in which the physiological characteristic sensor is coupled to the sensor carrier by the sensor retainer and the at least one retainer arm of the sensor retainer is in the second state.
Figure 25:
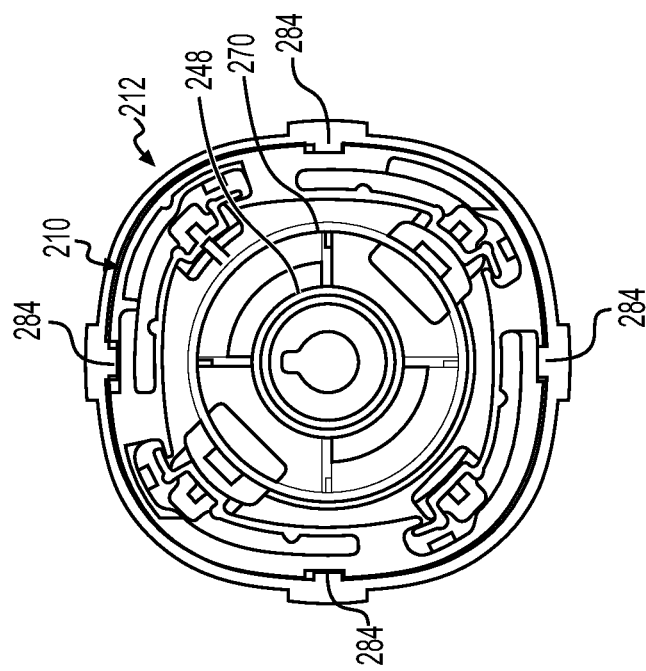
FIG. 25 is a cross-sectional view taken through the sensor carrier looking down at the sensor retainer, which illustrates the sensor retainer coupled to the sensor carrier.

With reference to FIG. 25, the retaining flange 272 is substantially rectangular in shape, and is coupled to the sensor retainer 210. The retaining flange 272 includes a plurality of retaining tabs 284 and defines a contact surface 286 (FIG. 26). The retaining tabs 284 couple the sensor retainer 210 to the sensor carrier 212. With reference to FIG. 26, the contact surface 286 is continuous and is defined about a perimeter of the retaining flange 272. The contact surface 286 presses the adhesive patch 120 (FIG. 22) against the anatomy of the user upon deployment of the physiological characteristic sensor 102 to ensure that the adhesive patch 120 is coupled to the user over an entirety of the adhesive patch 120. Thus, the contact surface 286 provides for improved adhesion of the adhesive patch 120 to the anatomy of the user.

Figure 27:
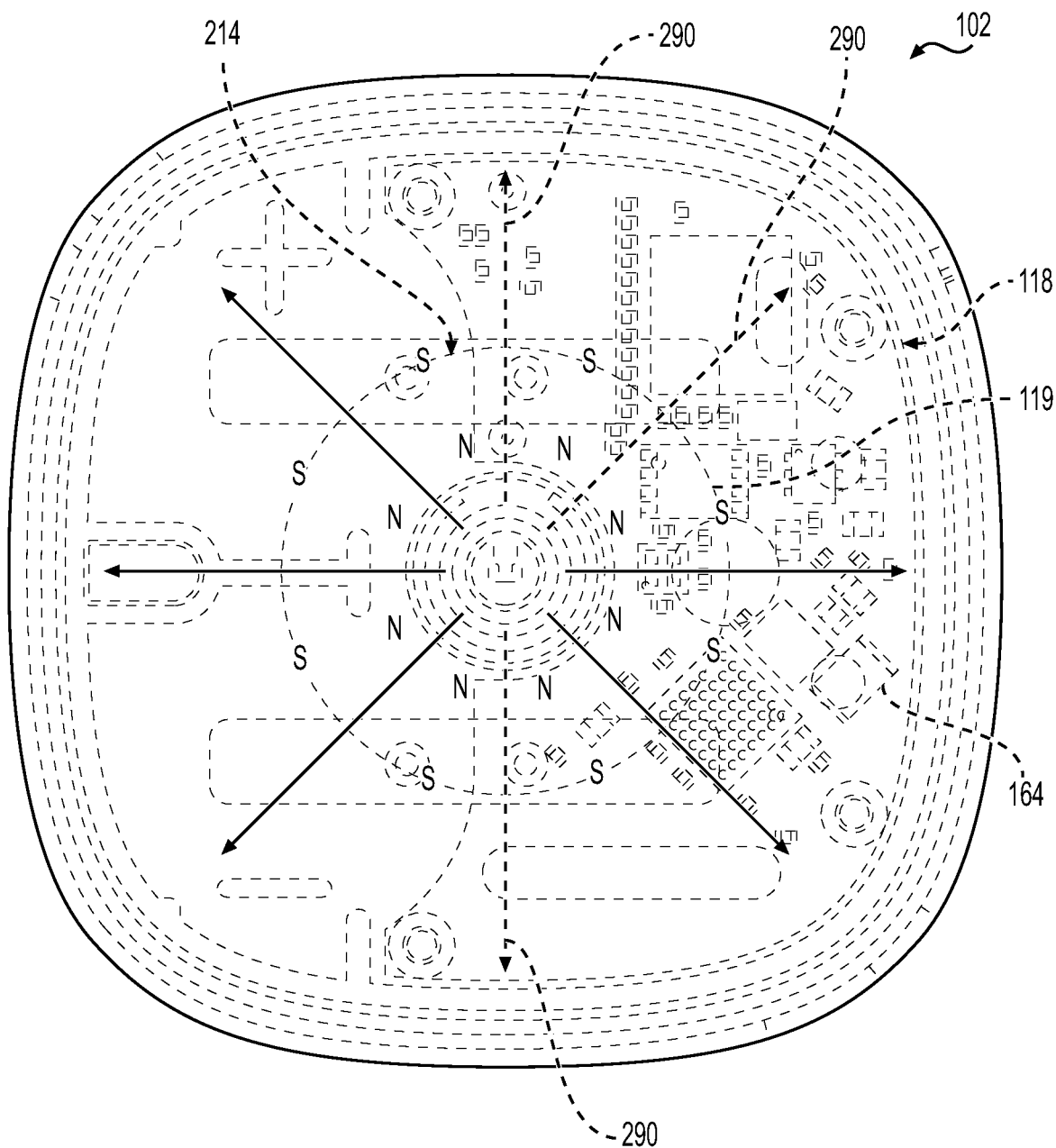
FIG. 27 is a schematic top view of the physiological characteristic sensor supported by the cap, which illustrates magnetic field lines associated with a magnet coupled to the cap.
Figure 28:
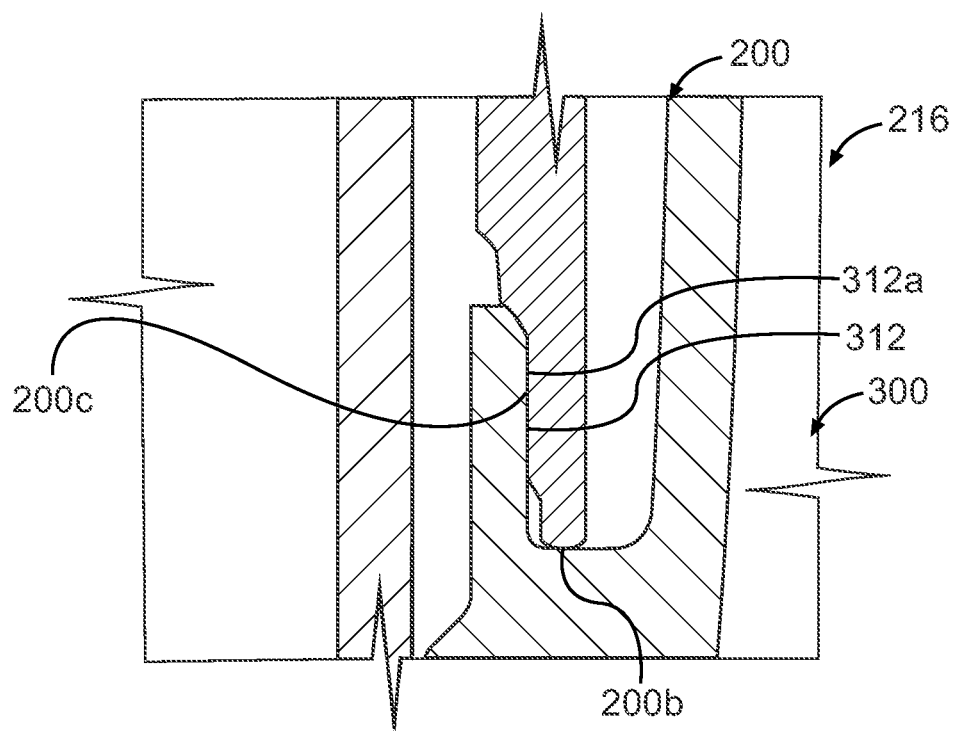
FIG. 28 is a detail view of an end of the plunger coupled to the cap with an interference fit to form a seal between the cap and the plunger.

With reference back to FIG. 14, the magnet 214 is coupled to the cap 216. In this example, the magnet 214 is annular to be coupled to the cap 216. The magnet 214 comprises any suitable permanent magnet composed of a ferromagnetic material that is axially magnetized. In one example, with reference to FIG. 27, the magnet 214 generates a three dimensional vector with radial component magnetic field lines 290, which cover a large percentage of the printed circuit board 164. By covering a large percentage of the printed circuit board 164, the magnet sensor 119 may be moved or repositioned on the printed circuit board 164 while remaining responsive to the magnetic field provided by the magnet 214. In addition, the radial component magnetic field lines 290 are axially symmetric, which results in the magnetic field being the same regardless of the axial position of the cap 216. This enables the cap 216 to be coupled to the plunger 200 at different final locations during assembly without affecting the magnetic field generated by the magnet 214. Thus, the magnet 214 also compensates for manufacturing tolerances, which reduces assembly time.

In this example, with reference to FIG. 24, the magnet 214 is coupled to the cap 216 via heat or ultrasonic welding, and may be retained within an annular channel 292 defined in a projection 294 of the cap 216. The annular channel 292 may include a lip 296, which extends over an uppermost surface of the magnet 214 to further assist in coupling the magnet 214 to the cap 216.

With reference to FIG. 2, the cap 216 may be composed of a biocompatible polymer, and may be molded, cast, printed, etc. The cap 216 includes the projection 294, a cap base 298 and a sidewall 300. The projection 294 extends axially upward from the cap base 298 and defines the annular channel 292 that is coupled to the magnet 214. With brief reference to FIG. 24, the projection 294 terminates in a tip 302. The tip 302 applies the force F3 against the bottom housing portion 124, which causes the insertion snaps 278 (FIG. 23) to float within the slots 246. The tip 302 is generally annular, such that the force F3 is distributed over an annular surface 302a and is not a point load. The tip 302 also enables the adhesive patch 120 of the physiological characteristic sensor 102 to be retained within the sensor inserter 104 without a backing layer. By eliminating the backing layer, the physiological characteristic sensor 102 is easier to deploy on the user.

With reference back to FIG. 2, the cap base 298 has a first base surface 304 opposite a second base surface 306 and defines a plurality of openings 308 (FIG. 14). The first base surface 304 is coupled to or integrally formed with the projection 294. The second base surface 306 defines a circular recess 310, which receives the membrane 218. The membrane 218 is a gas permeable polymeric material, such as Tyvek® manufactured by DuPont™ of Midland, Michigan, which is coupled to the cap 216 along a surface of the recess 310, via adhesives, heat bond, for example. The openings 308 are covered by the membrane 218. The openings 308 cooperate with the membrane 218 to enable the sterilization of the physiological characteristic sensor 102 contained within the sensor inserter 104. Generally, the plunger 200 and the cap 216 cooperate to form a seal, such that during a sterilization procedure, the sterilization gas may penetrate into and out of the sensor inserter 104, via the openings 308, and sterilize the physiological characteristic sensor 102 and an interior of the sensor inserter 104. In one example, with reference to FIG. 27, the bottom end 200b of the plunger 200 is coupled to the cap 216 in an interference fit, which inhibits fluids, such as air and liquids, to flow into the sensor inserter 104. In this example, the sidewall 300 of the cap 216 includes a lip 312, which circumscribes the cap 216 and receives the bottom end 200b of the plunger 200 with the interference fit. Generally, the bottom end 200b of the plunger 200 is deflected slightly to be received within the cap 216, which creates the interference fit between a surface 200c of the bottom end 200b and a surface 312a of the lip 312. The cap base 298 may also include a frame receiving channel 299, which receives the bottom end 208b of the frame 208. The frame receiving channel 299 generally mates tightly with the frame 208, which inhibits the frame 208 from deforming inward and disengaging with the cap 216 if the sensor inserter 104 is mishandled or dropped.

With reference back to FIG. 2, the sidewall 300 includes the lip 312, a plurality of threads 314 and a frame projection 316. The plurality of threads 314 are defined so as to be spaced apart from the lip 312. The plurality of threads 314 engage with the threads 236 of the plunger 200 to removably couple the cap 216 to the plunger 200. The frame projection 316 cooperates with a thread 208c defined on the frame 208 (FIG. 14). In one example, the frame projection 316 acts as a thread such that the cap 216 is screwed onto both the frame 208 and the plunger 200. By screwing the cap 216 onto both the frame 208 and the plunger 200, the frame 208 is locked in position relative to the plunger 200, which inhibits the frame 208 from moving relative to the plunger 200 in an instance where the sensor inserter 104 is mishandled or dropped.

Figure 29:
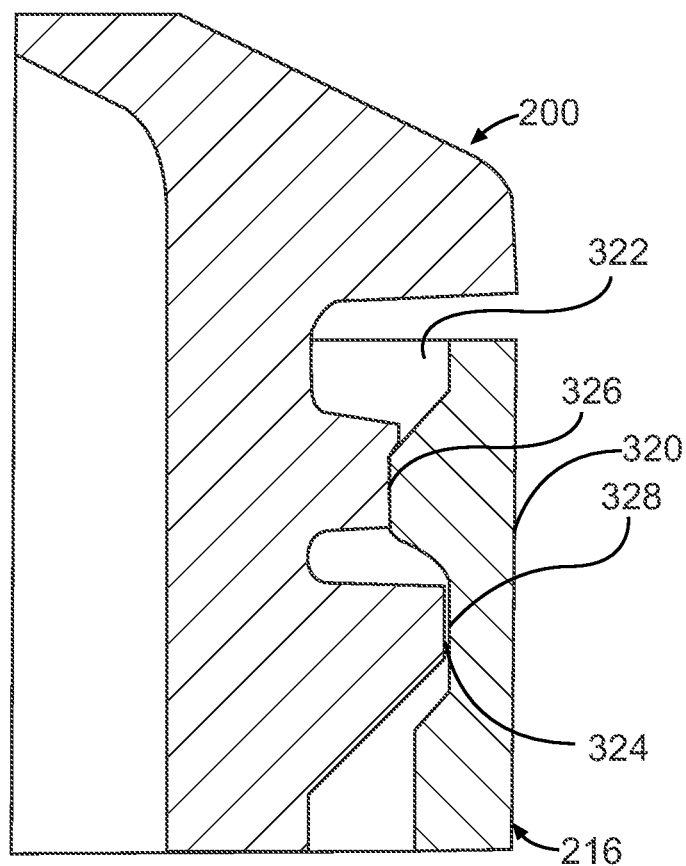
FIG. 29 is a detail view of a tamper evident band coupled to the cap and to the plunger.

In one example, the cap 216 also includes a tamper evident band or tamper band 320. The tamper band 320 may be composed of a biocompatible polymer, and may be molded, cast, additive manufactured, etc. The tamper band 320 may be coupled to the cap 216 via a plurality of bridges 320a (FIG. 1), which are breakable upon unscrewing or uncoupling the cap 216 from the plunger 200. The tamper band 320 may be integrally formed with the cap 216, and the bridges 320a (FIG. 1) may be defined through a post processing step. The tamper band 320 provides a visual indicator as to whether or not the cap 216 has been removed from the plunger 200. In this example, the plunger 200 also define a tamper bead retaining wall 322 and a tamper bead retaining catch 324 about an outer perimeter of the plunger 200. With reference to FIG. 29, the tamper bead retaining wall 322 receives a corresponding tamper bead 326 defined on the tamper band 320. The tamper bead retaining catch 324 extends outward for a distance greater than the tamper bead retaining wall 322 and is received in a corresponding groove 328. The tamper bead 326 on the tamper band 320 vertically overlaps the tamper bead retaining catch 324 such that as the user is removing the cap 216, the tamper bead 326 of the tamper band 320 contacts the tamper bead retaining catch 324. The contact between the tamper bead 326 and the tamper bead retaining catch 324, along with the continued applied force by the user, separates the cap 216 from the tamper band 320 at the bridges 320a (FIG. 1), leaving the tamper band 320 about the plunger 200 to visually indicate the cap 216 has been removed.

In one example, with reference to FIG. 14, in order to assemble the sensor inserter 104, the needle inserter 198 is coupled to the physiological characteristic sensor 102. The retraction spring 206 is positioned about the needle inserter 198. The needle inserter 198 is coupled to the needle retractor 204 such that the retraction spring 206 is disposed about the needle retractor 204. The sensor carrier 212 is coupled to the needle retractor 204, and the sensor retainer 210 is coupled to the sensor carrier 212. The frame 208 is coupled to the sensor carrier 212. The insertion spring 202 is coupled to the sensor carrier 212, and the plunger 200 is coupled to the frame 208. The cap 216, with the membrane 218 and the tamper band 320 coupled to the cap 216, is threaded onto the plunger 200. The sensor inserter 104, including the physiological characteristic sensor 102, may be sterilized and shipped to an end user.

Figure 31:
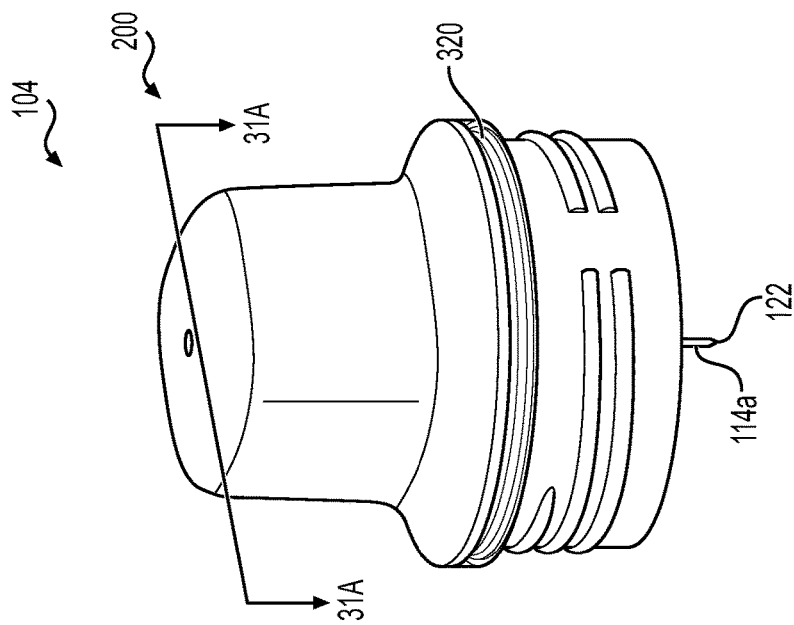
FIG. 31 is a perspective view of the sensor inserter in a second position, in which the sensor inserter is positioned over the insertion site and the plunger is depressed by the user to deploy the physiological characteristic sensor onto and into the anatomy.
Figure 30:
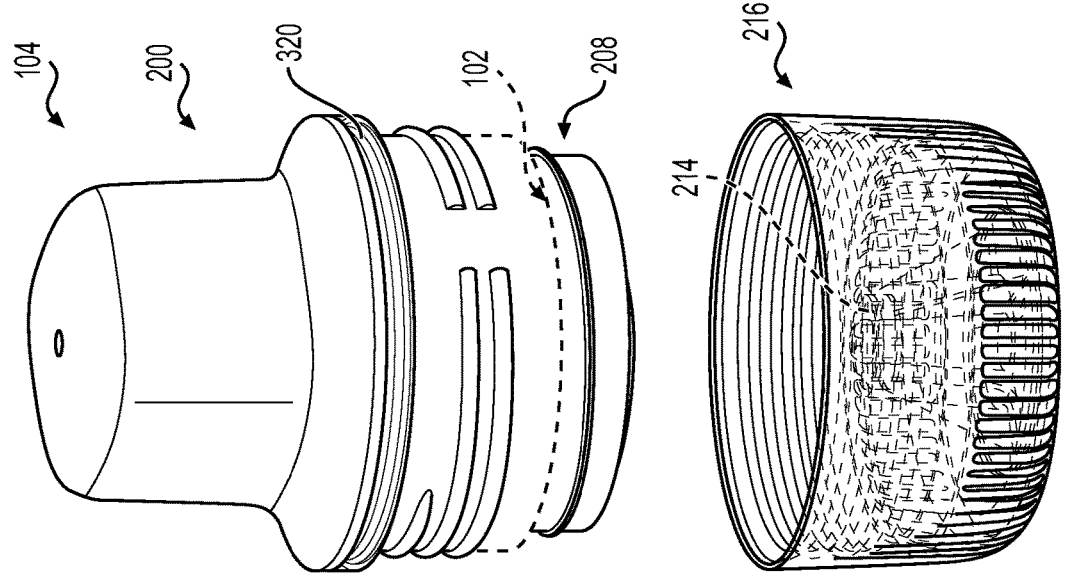
FIG. 30 is a perspective view of the sensor inserter in the first position, in which the cap is removed prior to coupling the physiological characteristic sensor to an insertion site on a portion of an anatomy.

Once received, with reference to FIG. 30, the user may remove the cap 216. As the user unscrews the cap 216, the tamper band 320 breaks along the bridges 320a (FIG. 1) and remains coupled to the plunger 200. With the cap 216 removed, the physiological characteristic sensor 102 is exposed for insertion. In addition, the removal of the cap 216 removes the magnetic field generated by the magnet 214. Based on the sensor signals from the magnet sensor 119 (FIG. 3), the control module 162 (FIG. 3) begins to monitor the sensor signals from the glucose sensor 114 (FIG. 3). Stated another way, the removal of the cap 216 activates the physiological characteristic sensor 102 to monitor the glucose sensor 114 and transmit the blood glucose levels via the antenna 108, 108'. With reference to FIG. 31, the user may position the sensor inserter 104 at the desired insertion site, which may or may not be visible to the user. The user may depress the plunger 200, which releases the sensor carrier 212 (FIG. 14) and the retainer arms 266 of the sensor retainer 210 (FIG. 14). The release of the sensor carrier 212 and the retainer arms 266 (FIG. 14) separates the physiological characteristic sensor 102 from the sensor inserter 104. Once the sensor carrier 212 is released from the frame 208 (FIG. 14), the insertion spring 202 applies the force F1 to couple the physiological characteristic sensor 102 to the user, as shown in FIG. 31A. The sensor inserter 104 is in the second position in FIG. 31A.

Generally, with reference to FIG. 31B, once the insertion spring 202 deploys the sensor carrier 212, the retraction spring 206 applies the force F2 (FIG. 2) and retracts the needle retractor 204 upward, which in turn, retracts the needle inserter 198 (FIG. 14) into the plunger 200. In FIG. 31B, the sensor inserter 104 is in the third position. This inhibits the user accidentally contacting the insertion needle 222 (FIG. 14) and inhibits a reuse of the sensor inserter 104. With reference to FIGS. 32 and 32A, once the physiological characteristic sensor 102 is coupled to the user at the insertion site, the sensor inserter 104 is removed from the insertion site and disposed of. The sensor inserter 104 remains in the third position in FIGS. 32 and 32A.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A physiological characteristic sensor system, comprising:
  a physiological characteristic sensor that includes a housing having a first housing portion coupled to a second housing portion, an antenna, and a sensor, the second housing portion having a bottom region and a sidewall extending upwardly from the bottom region, wherein the first housing portion and the second housing portion cooperate to enclose the antenna and a portion of the sensor, the antenna is coupled to the first housing portion to face a first surface of the second housing portion, and the portion of the sensor is coupled to the first surface; and
  a sensor inserter configured to be coupled to the physiological characteristic sensor, the sensor inserter including a sensor retainer that is configured to couple to the sidewall of the second housing portion in a second state while the second housing portion is at least partially inside the sensor inserter and configured to be uncoupled from the second housing portion in a first state while the second housing portion is at least partially inside the sensor inserter, the sensor retainer including a central bore configured to receive the housing of the physiological characteristic sensor and a plurality of retainer arms spaced apart about a perimeter of the central bore to surround the housing of the physiological characteristic sensor, each retainer arm of the plurality of retainer arms is movable between the first state and the second state, in the first state, a terminal end of each retainer arm of the plurality of retainer arms is spaced apart from a surface of the sensor retainer to define a gap, and in the second state, the terminal end of each retainer arm of the plurality of retainer arms contacts the surface of the sensor retainer.

2. The physiological characteristic sensor system of claim 1, wherein the sensor inserter comprises a plunger movable relative to a frame and a sensor carrier coupled to the frame, and the sensor retainer is coupled to the sensor carrier.

3. The physiological characteristic sensor system of claim 2, wherein the frame has at least one rib that maintains the sensor retainer in the second state.

4. The physiological characteristic sensor system of claim 2, wherein the sensor inserter comprises a cap, and the cap is threadably coupled to the plunger and the frame such that the cap forms an interference fit with an end of the plunger.

5. The physiological characteristic sensor system of claim 4, wherein the cap further comprises a tamper evident band having a plurality of bridges that couple the cap to the tamper evident band and are configured to break upon removal of the cap from the plunger.

6. The physiological characteristic sensor system of claim 4, wherein the cap further comprises a magnet that is axially magnetized to generate a magnetic field, and the physiological characteristic sensor includes a magnet sensor responsive to the magnetic field.

7. The physiological characteristic sensor system of claim 2, wherein the sensor carrier includes a retaining flange having a plurality of retaining tabs and a first retaining surface that is continuous about a perimeter of the retaining flange configured to press an adhesive patch associated with the physiological characteristic sensor to an anatomy, the plurality of retaining tabs couple the sensor carrier to the sensor retainer such that the sensor retainer is coupled to a second retaining surface of the sensor carrier, the second retaining surface opposite the first retaining surface, and the adhesive patch is coupled to the bottom region of the second housing portion.

8. The physiological characteristic sensor system of claim 1, wherein a printed circuit board assembly is coupled to the first surface of the second housing portion, and the printed circuit board assembly includes at least one spring contact to electrically couple the antenna to the printed circuit board assembly.

9. The physiological characteristic sensor system of claim 8, wherein the first housing portion includes a first contact, a second contact is coupled to the printed circuit board assembly and at least one battery is coupled to the second contact and the second housing portion.

10. The physiological characteristic sensor system of claim 9, wherein the first contact includes a pair of spring arms that are interconnected by a body, and the body is coupled to the first housing portion such that the pair of spring arms are movable relative to the body.

11. The physiological characteristic sensor system of claim 1, wherein the sensor is a glucose sensor, a sealing member is coupled between a distal end of the glucose sensor and the first housing portion, and a second sealing member is coupled between the distal end of the glucose sensor and the second housing portion.

12. The physiological characteristic sensor system of claim 11, wherein the first housing portion includes a first angled surface that compresses the sealing member to form a seal and the second housing portion includes a second angled surface that compresses the second sealing member to form a second seal.

13. The physiological characteristic sensor system of claim 1, wherein each retainer arm of the plurality of retainer arms includes a contact surface spaced apart from the terminal end that is configured to contact the sidewall of the second housing portion of the physiological characteristic sensor to couple the physiological characteristic sensor to the sensor retainer in the second state.

14. A physiological characteristic sensor system, comprising:
a physiological characteristic sensor that includes a housing having a first housing portion coupled to a second housing portion and a sensor, the second housing portion having a bottom region and a sidewall extending upwardly from the bottom region, wherein the first housing portion and the second housing portion cooperate to enclose a portion of the sensor, and the portion of the sensor is coupled to a first surface of the second housing portion; and
a sensor inserter configured to be coupled to the physiological characteristic sensor, the sensor inserter including a frame, a sensor carrier and a sensor retainer, the sensor carrier including a retaining flange, the sensor retainer coupled to the sensor carrier so as to be received within the retaining flange, and the sensor carrier coupled to the frame, the frame having a plurality of ribs spaced apart about an inner perimeter of the frame, the sensor retainer including a central bore configured to receive the housing of the physiological characteristic sensor and a plurality of retainer arms spaced apart about a perimeter of the central bore to surround the housing of the physiological characteristic sensor, the plurality of retainer arms configured to couple to the sidewall extending upwardly from the bottom region of the second housing portion in a second state while the second housing portion is at least partially inside the sensor inserter and configured to be uncoupled from the second housing portion in a first state while the second housing portion is at least partially inside the sensor inserter, each retainer arm of the plurality of retainer arms is movable between the first state and the second state, in the first state, a terminal end of each retainer arm of the plurality of retainer arms is spaced apart from a surface of the sensor retainer to define a gap, in the second state, the terminal end of each retainer arm of the plurality of retainer arms contacts the surface of the sensor retainer, and each rib of the plurality of ribs biases a respective retainer arm of the plurality of retainer arms to eliminate the gap in the second state.

15. The physiological characteristic sensor system of claim 14, wherein the sensor inserter comprises a plunger movable relative to the frame and a cap, the cap is threadably coupled to the plunger and the frame such that the cap forms an interference fit with an end of the plunger, and the cap further comprises a tamper evident band having a plurality of bridges that couple the cap to the tamper evident band and are configured to break upon removal of the cap from the plunger.

16. The physiological characteristic sensor system of claim 15, wherein the cap further comprises a magnet that is axially magnetized to generate a magnetic field, and the physiological characteristic sensor includes a magnet sensor responsive to the magnetic field.

17. The physiological characteristic sensor system of claim 14, wherein each retainer arm of the plurality of retainer arms includes a contact surface spaced apart from the terminal end that is configured to contact the sidewall of the second housing portion of the physiological characteristic sensor to couple the physiological characteristic sensor to the sensor retainer in the second state.

18. A physiological characteristic sensor system, comprising:
a physiological characteristic sensor that includes a housing having a first housing portion coupled to a second housing portion, a sensor, an antenna, a printed circuit board assembly, and a battery, the second housing portion having a bottom region and a sidewall extending upwardly from the bottom region, wherein the first housing portion and the second housing portion cooperate to enclose a portion of the sensor, the antenna, the printed circuit board assembly and the battery, the antenna and a first contact are coupled to the first housing portion, the printed circuit board assembly and the battery are coupled to a first surface of the second housing portion, the portion of the sensor is coupled to the printed circuit board assembly and the first surface of the second housing portion, the antenna and the battery are in communication with the printed circuit board assembly, the first contact includes a pair of spring arms that are interconnected by a body, and the body is coupled to the first housing portion such that the pair of spring arms are movable relative to the body, and the physiological characteristic sensor includes an adhesive patch coupled to the bottom region of the second housing portion; and
a sensor inserter configured to be coupled to the physiological characteristic sensor, the sensor inserter including a sensor retainer that is configured to couple to the sidewall of the second housing portion in a second state while the second housing portion is at least partially inside the sensor inserter and configured to be uncoupled from the second housing portion in a first state while the second housing portion is at least partially inside the sensor inserter, the sensor retainer including a central bore configured to receive the housing of the physiological characteristic sensor and a plurality of retainer arms spaced apart about a perimeter of the central bore to surround the housing of the physiological characteristic sensor, each retainer arm of the plurality of retainer arms is movable between the first state and the second state, in the first state, a terminal end of each retainer arm of the plurality of retainer arms is spaced apart from a surface of the sensor retainer to define a gap, and in the second state, the terminal end of each retainer arm of the plurality of retainer arms contacts the surface of the sensor retainer.

19. The physiological characteristic sensor system of claim 18, wherein the antenna includes at least one spring contact that contacts the printed circuit board assembly to enable communication between the antenna and the printed circuit board assembly.

\* \* \* \* \*